US008632972B2

(12) United States Patent
Eberwine et al.

(10) Patent No.: US 8,632,972 B2
(45) Date of Patent: *Jan. 21, 2014

(54) METHODS AND COMPOSITIONS FOR IDENTIFYING RNA-BINDING PROTEINS

(75) Inventors: James Eberwine, Philadelphia, PA (US); Ulo Langel, Bandhagen (SE); Kalle Kilk, Danderyd (SE); Jennifer Zielinski, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1746 days.

This patent is subject to a terminal disclaimer.

(21) Appl. No.: 11/472,097

(22) Filed: Jun. 20, 2006

(65) Prior Publication Data

US 2008/0199854 A1 Aug. 21, 2008

Related U.S. Application Data

(63) Continuation of application No. PCT/US2004/043401, filed on Dec. 22, 2004.

(60) Provisional application No. 60/531,719, filed on Dec. 22, 2003.

(51) Int. Cl.
*C12Q 1/68* (2006.01)
*C07K 7/00* (2006.01)
*C07H 21/00* (2006.01)

(52) U.S. Cl.
USPC ......... 435/6.11; 435/6.19; 536/24.1; 530/326

(58) Field of Classification Search
USPC ................. 435/6.11, 6.19; 530/326; 536/24.1
See application file for complete search history.

(56) References Cited

U.S. PATENT DOCUMENTS

| | | | |
|---|---|---|---|
| 4,415,732 A | 11/1983 | Caruthers et al. | |
| 4,458,066 A | 7/1984 | Caruthers et al. | |
| 5,013,830 A | 5/1991 | Ohtsuka et al. | |
| 5,188,934 A | 2/1993 | Menchen et al. | |
| 5,366,860 A | 11/1994 | Bergot et al. | |
| 6,025,140 A * | 2/2000 | Langel et al. | 435/6 |
| 6,180,370 B1 | 1/2001 | Queen et al. | |
| 7,223,833 B1 * | 5/2007 | Nielsen et al. | 530/300 |

FOREIGN PATENT DOCUMENTS

| WO | WO99/05302 | 2/1999 | | |
|---|---|---|---|---|
| WO | WO 03/092736 | * 11/2003 | ............ | A61K 47/48 |

OTHER PUBLICATIONS

Tannenbaum et al., 2000, PNAS 97(26): 14085-14090.*
Akhtar, E., et al., 1991, Life Sciences 49:1793-1801.
Azhayeva, E., et al., Nucleic Acids Res., 23:1170-76 (1995).
Barbas, 1995, Nature Medicine 1:837-839.
Bartfai, T. Galanin: A neuropeptide with important CNS actions. In: Psychopharmacology: The Fourth Generation of Progress (F.E. Bloom and D.J. Kupfer, eds.) Raven Press, Ltd., New York, pp. 563-571 (1995).
Beaucage, S. L., et al., Tetrahedron, 48:2223-2311 (1992).
Bennett, C., Biochem. Pharmacol., 55:9-19 (1998).
Braslawsky et al., 1991, Cancer Immunol Immunother. 33:367-74.
Brodsky, A.S., et al., Molecular & Cellular Proteomics, 1.12, 922-9 (2002).
Burton et al., 1994, Adv. Immunol. 57:191-280.
Cardullo et al., 1988, PNAS 85:8790-8794.
Clegg, 1992, Meth. Enzymol. 211:353-388.
de Kruif et al. 1995, J. Mol. Biol. 248:97-105.
Demidov, V., et al., Biochem. Pharmacol., 48:1310-13 (1994).
Derossi et al., 1994, J Biol Chem 269:10444-10450.
Egholm, M., et al., Nature, 365:566-68 (1993).
Eiriksdottir et al., 2004, Drug Design Reviews 1:161-173.
Fletcher et al., 2004, Org Lett. 6:4245-4248.
Gillam and Smith, Gene, 8:81-97 (1979).
Goodchild, J., Nucleic Acids Research, 20:4607-12 (1992).
Grether et al., 2001, Chemistry 7:959-971.
Gu et al. (1997), Thrombosis and Hematocyst 77: 755-759.
Habert-Ortoli, E., et al., Proc. Natl. Acad. Sci. USA, 91:9780-83 (1994).
Hallbrink et al (2001), Biochim Biophys Acta. 1515:101-9.
Hanvey, J., et al., Science 258:1481-1485 (1992).
Kilk et al., 2004, Neuropeptides 38:316-324.
Knudsen, H., et al., Anticancer Drug, 8;113-18 (1997).
Knudsen, H., et al., Nucl. Acids Res., 24:494-500 (1996).
Koch T., et al., J. Pept. Res., Jan;49(1):80-8 (1997).
Lamond, A., et al., Cell, 58:383-90 (1989).
Loakes, D., et al., Nucleic Acids Research, 22:4039-43 (1994).
Marks et al. (1991), J. Mol. Biol. 222:581-597.
Miyashiro, K. Y. et al., Neuron, 37, 417-31 (2003).
Morvan F., et al., Nucleic Acids Research, 14:5019-35 (1986).
Nichols, R., et al., Nature, 369:492-3 (1994).
Nielsen, P. E., et al., Anti-Cancer Drug Design, 8:53-63 (1993).
Nielsen, P. E., et al., Science, 254:1497-1500 (1991).
Peffer, N., et al., Proc. Natl. Acad. Sci. USA, 90:10648-52 (1993).
Perbost et al., Biochem. Biophys. Res. Comm., 165:742—(1989).
Pooga et al., 1998, FASEB J. 12:67-77.
Pooga M., et al., Methods Mol. Biol., 208:225-36 (2002).
Pooga, M., et al., FASEB J., 15, 1451-1453 (2001).
Pooga, M., et al., Nat. Biotechnol., 16, 857-61 (1998).
Roberts et al., 1987, Nature, 328:731-734.
Tenenbaum, S.A., et al., PNAS, 97, 14085-90 (2000).
Tuszynski et al. (1988), Blood, 72:109-115.
Vives et al., (1997), J Biol Chem 272:16010-16017.
Wright et al. (1992), Critical Rev. Immunol. 12:125-168.
Zielinski et al., 2006, Proc Natl Acad Sci 103:1557-1562.

* cited by examiner

*Primary Examiner* — Amber D Steele
(74) *Attorney, Agent, or Firm* — Riverside Law LLP

(57) ABSTRACT

The present invention includes compositions, methods and kits for the identification of a polypeptide that binds to a predetermined RNA sequence. The invention comprises, in part, a photoreactive moiety to aid in identification of such a polypeptide.

5 Claims, 4 Drawing Sheets

Glutamate Receptor Photoactivatable Cross-linking PNA
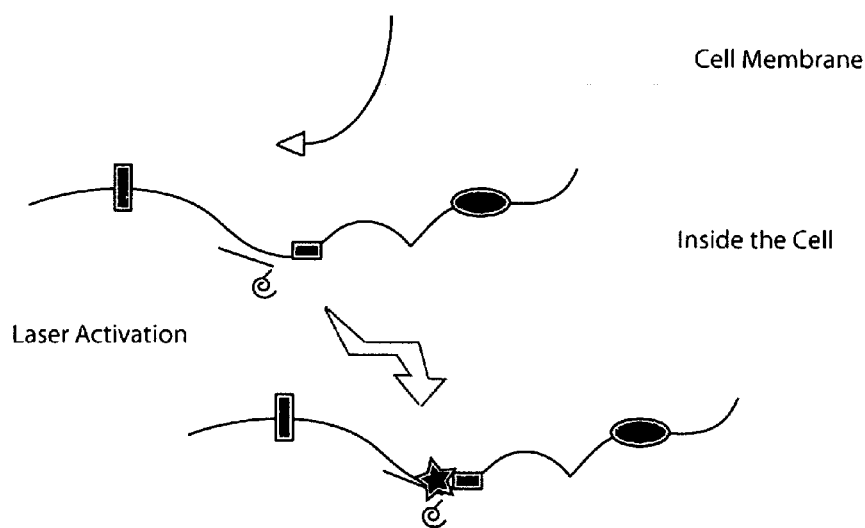
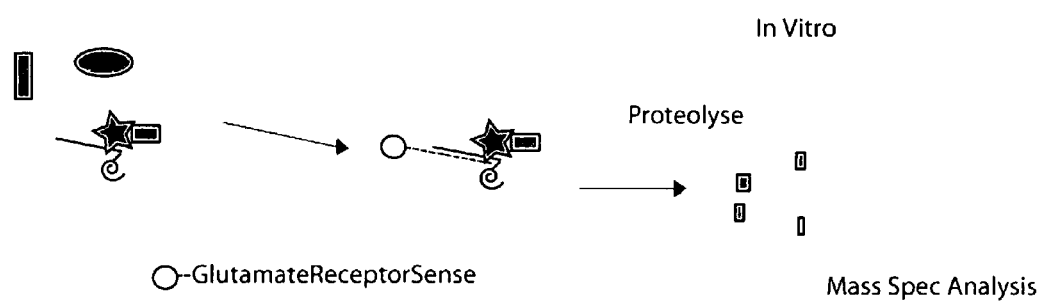
Fig. 1

```
-300  ggcacgaggccgctgtcagcagaagcctctgctgccgccgccgccgccactgccgctgtccctgtccctcctctctttctcccc
-216  ggcagatctttgttgtgtgggagggcagcggggatggacttgagctcgcggctcttctgctagagcagccgcgcttggagagga         ——— Ank 3
-132  cgccgccgccgcgagcagccgccgcccccaggccccgccagccgcggcctccgtccccgcgccgcgctccgcgcgcctcccagca
-48   cagtgccctcgcggcggcagatgagtgtggggtcagcccacggcggggatggtgaaattcccggcgctcacgcactactggccc
1                                                   M  V  K  F  P  A  L  T  H  Y  W  P
+37   ctgatccggttcctggtgcccttggcatcaccaacatagccatcgacttcggggagcaggccttgaaccggggcattgctgca
13     L  I  R  F  L  V  P  L  G  I  T  N  I  A  I  D  F  G  E  Q  A  L  N  R  G  I  A  A
+121  gtcaaggaagatgcagtagagatgctggccagctatgggctggcgtattctctgatgaagttcttcgcggggaccatgagtgac
41     V  K  E  D  A  V  E  M  L  A  S  Y  G  L  A  Y  S  L  M  K  F  F  A  G  P  M  S  D
+205  ttcaagaatgtgggcctggtgtttgtgaacagcaagagagacagggccaaagctgtcctgtgcatggtggtggccggtgccatt
69     F  K  N  V  G  L  V  F  V  N  S  K  R  D  R  A  K  A  V  L  C  M  V  V  A  G  A  I
+289  gctgcagtcttccacaccctgatagcctacagtgacttagggtactacatcatcaacaagctacatcatgtggacgagtctgtg
97     A  A  V  F  H  T  L  I  A  Y  S  D  L  G  Y  Y  I  I  N  K  L  H  H  V  D  E  S  V
+373  gggagcaaaacacgaagggccttcctgtatctcgctgcctttcccttttatggatgccatggcgtggactcatgctggcattctc
125    G  S  K  T  R  R  A  F  L  Y  L  A  A  F  P  F  M  D  A  M  A  W  T  H  A  G  I  L
+457  ttaaaacacaaatacagtttcctggtgggatgtgcctcaatctcagatgtcatagctcaggttgtgttcgtagccattttactt
153    L  K  H  K  Y  S  F  L  V  G  C  A  S  I  S  D  V  I  A  Q  V  V  F  V  A  I  L  L
+541  cacagtcacctggaatgccgagagccgctgctcatccccatcctgtctctgtacatgggtgcacttgtgcgctgtaccacgctg
181    H  S  H  L  E  C  R  E  P  L  L  I  P  I  L  S  L  Y  M  G  A  L  V  R  C  T  T  L
+625  tgcctgggctactacaggaacatccacgacatcatccctgacaggagcggcccagagctgggggcgacgcaaccataagaaag
209    C  L  G  Y  Y  R  N  I  H  D  I  I  P  D  R  S  G  P  E  L  G  G  D  A  T  I  R  K
+709  atgctgagcttctggtggcctctggctctgattctggccacgcagcgcatcagccggcccattgtcaacctctttgtgtcccgg
237    M  L  S  F  W  W  P  L  A  L  I  L  A  T  Q  R  I  S  R  P  I  V  N  L  F  V  S  R
+793  gatcttggtggcagttctgctgctacagaggcagtggccattctgacagctacctacccgtgggtcacatgccatatggctgg
265    D  L  G  G  S  S  A  A  T  E  A  V  A  I  L  T  A  T  Y  P  V  G  H  M  P  Y  G  W
+877  ttgacagaaatccgtgctgtctaccctgcttttgacaagaataaccccagcaataaactggccaacacgaacaacacggtcacc
293    L  T  E  I  R  A  V  Y  P  A  F  D  K  N  N  P  S  N  K  L  A  N  T  N  N  T  V  T
+961  tcggcccacatcaagaagttcaccttcgtctgcatggcactgtcactgacgctctgttttgtaatgttctggaccccaacgtc
321    S  A  H  I  K  K  F  T  F  V  C  M  A  L  S  L  T  L  C  F  V  M  F  W  T  P  N  V
+1045 tctgagaagatttttgatagacatcattggagtggacttcgcctttgcagaactctgtgtcattcctctgcgtatcttctccttc
349    S  E  K  I  L  I  D  I  I  G  V  D  F  A  F  A  E  L  C  V  I  P  L  R  I  F  S  F
+1129 ttcccagtgccagtgactgtgagagctcatctcactggatggttgatgacacttaagaaaacctttgttctggcaccagctcc
377    F  P  V  P  V  T  V  R  A  H  L  T  G  W  L  M  T  L  K  K  T  F  V  L  A  P  S  S
+1213 gtgctgcggatcatcgtcctcatcaccagccttgtggttctgccttacctggggggtgcatggagccacactaggtgtgggctcc
405    V  L  R  I  I  V  L  I  T  S  L  V  V  L  P  Y  L  G  V  H  G  A  T  L  G  V  G  S
+1297 cttctagcagggtttgtgggagagtctaccatggttgccctcgcagcatgctatgtgtatcggaagcagaaaaagaagatggag
433    L  L  A  G  F  V  G  E  S  T  M  V  A  L  A  A  C  Y  V  Y  R  K  Q  K  K  K  M  E
+1381 aatgagtcagccaccgaggggaagactcggccatgaccgacatgcctccagcagaggaggtgacagacatcgtagagatgaga
461    N  E  S  A  T  E  G  E  D  S  A  M  T  D  M  P  P  A  E  E  V  T  D  I  V  E  M  R
+1465 gaggaaaatgagtaagcacgggccaccaggggcactacagggacagtcaggacaacagtcgtctcttccctcctcctcccacca
489    E  E  N  E  *                                ━━━━━━━━━━━━━━━━━━━━━━━━━━━━            ——— Ank 2
+1549 agttgtttctgttgtttaattttattcttggttatgaaagaggccttgatttagaggtttcgtataaattctctagcatact
                                                           ━━━━━━━━━━━━━━━━━━━━━━━━━━━━     ——— Ank 1
+1633 gggtatgctcaccgatgcagggacctgaagaaaggtctttactgtcgctttgtaactcagaactgctgacttcatgcccctgcc
+1717 tcacaaaacccaaaagatagagctgcctcttggccgacaatctccactttggaaccaaaggacttgg
+1801 gctgtgccgctgcctcttgggccagactctttttccgttcgtgttttgtctcctaagaatcaacaggttgaagctcagcctctctt
+1885 gacttgctccccaataatgtggctctaagacacgtgacccggtggccatcacacccctttttcactctagagtcaagaactgtct
+1969 gcagcgcccactggtgggcccaggctgcagcccacagtctccctgctcccagaggaagagctggtagccatgttgggccaaca
+2053 taatgggaaatttaatctcctgtagaaattggatcagtcacaaactgacttgatcgccagcatctcattgttttcctggtttcg
+2137 ctgagttgccacgcccctcgtgccg
```

Fig. 2

SEQUENCE LISTING

<160> NUMBER OF SEQ ID NOS: 11

<210> SEQ ID NO 1

<400> SEQUENCE: 1

000

<210> SEQ ID NO 2
<211> LENGTH: 21
<212> TYPE: PRT
<213> ORGANISM: Artificial Sequence
<220> FEATURE:
<223> OTHER INFORMATION: A truncated version of SEQ ID NO:6 having 6 aa
      of galanin (Rattus norvegicus) for its N-terminal end, the entire
      14 aa mastoparan peptide (Vespula lewisii) for its C-terminal end,
      and a lysine residue in the 13th position linking the two ends

<400> SEQUENCE: 2

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 3
<211> LENGTH: 21
<212> TYPE: DNA
<213> ORGANISM: Rattus norvegicus

<400> SEQUENCE: 3
tacgaaacct ctaaatcaag g                                          21

<210> SEQ ID NO 4
<211> LENGTH: 21
<212> TYPE: DNA
<213> ORGANISM: Rattus norvegicus

<400> SEQUENCE: 4
aaacctctaa atcaaggcct c                                          21

<210> SEQ ID NO 5
<211> LENGTH: 22
<212> TYPE: DNA
<213> ORGANISM: Rattus norvegicus

<400> SEQUENCE: 5
aagcgcggct gctctagcag aa                                         22

<210> SEQ ID NO 6
<211> LENGTH: 27
<212> TYPE: PRT
<213> ORGANISM: Artificial Sequence
<220> FEATURE:
<223> OTHER INFORMATION: A synthetic peptide having the first 12 N-
      terminal aa of galanin (Rattus norvegicus) for its N-terminal end,
      the entire 14 aa mastoparan peptide (Vespula lewisii) for its C-
      terminal end, and a lysine residue in the 13th position linking
      the two ends

<400> SEQUENCE: 6

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

-continued

```
<210> SEQ ID NO 7
<211> LENGTH: 16
<212> TYPE: PRT
<213> ORGANISM: Drosophila melanogaster

<400> SEQUENCE: 7

Arg Gln Ile Lys Ile Trp Phe Gln Asn Arg Arg Met Lys Trp Lys Lys
1               5                   10                  15

<210> SEQ ID NO 8
<211> LENGTH: 13
<212> TYPE: PRT
<213> ORGANISM: Human immunodeficiency virus type 1

<400> SEQUENCE: 8

Gly Arg Lys Lys Arg Arg Gln Arg Arg Arg Pro Pro Gln
1               5                   10

<210> SEQ ID NO 9
<211> LENGTH: 7
<212> TYPE: PRT
<213> ORGANISM: Simian virus 40

<400> SEQUENCE: 9

Pro Lys Lys Lys Arg Lys Val
1               5

<210> SEQ ID NO 10
<211> LENGTH: 2464
<212> TYPE: DNA
<213> ORGANISM: Rattus norvegicus

<400> SEQUENCE: 10
ggcacgaggc cgctgtcagc agaagcctct gctgccgccg ccgccgccac tgccgctgtc      60
cctgtccctc ctctctttct ccccggcaga tctttgttgt gtgggagggc agcggggatg     120
gacttgagct cgcggctctt ctgctagagc agccgcgctt ggagaggacg ccgccgccgc     180
gagcagccgc cgccccaggc cccgccagcc gcggcctccg tccccgcgcc cgctccgcg      240
cgcctcccag cacagtgccc tcgcggcggc agatgagtgt ggggtcagcc cacggcgggg     300
actatggtga aattcccggc gctcacgcac tactggcccc tgatccggtt cctggtgccc     360
cttggcatca ccaacatagc catcgacttc ggggagcagg ccttgaaccg gggcattgct     420
gcagtcaagg aagatgcagt agagatgctg ccagctatg gctggcgta ttctctgatg      480
aagttcttcg cgggacccat gagtgacttc aagaatgtgg gcctggtgtt tgtgaacagc     540
aagagagaca gggccaaagc tgtcctgtgc atggtggtgg ccggtgccat tgctgcagtc     600
ttccacaccc tgatagccta cagtgactta gggtactaca tcatcaacaa gctacatcat     660
gtggacgagt ctgtggggag caaaacacga agggccttcc tgtatctcgc tgccttccct     720
tttatggatg ccatggcgtg gactcatgct ggcattctct aaaacacaa atacagtttc     780
ctggtgggat gtgcctcaat ctcagatgtc atagctcagg ttgtgttcgt agccatttta     840
cttcacagtc acctggaatg ccgagagccg ctgctcatcc ccatcctgtc tctgtacatg     900
ggtgcacttg tgcgctgtac cacgctgtgc ctgggctact acaggaacat ccacgacatc     960
atccctgaca ggagcggccc agagctgggg ggcgacgcaa ccataagaaa gatgctgagc    1020
ttctggtggc ctctggctct gattctggcc acgcagcgca tcagccggcc cattgtcaac    1080
ctctttgtgt cccgggatct tggtggcagt tctgctgcta cagaggcagt ggccattctg    1140
acagctacct accccgtggg tcacatgcca tatggctggt tgacagaaat ccgtgctgtc    1200
```

-continued

```
taccctgctt tgacaagaa taaccccagc aataaactgg ccaacacgaa caacacggtc    1260
acctcggccc acatcaagaa gttcaccttc gtctgcatgg cactgtcact gacgctctgt    1320
tttgtaatgt tctggacccc caacgtctct gagaagattt tgatagacat cattggagtg    1380
gacttcgcct ttgcagaact ctgtgtcatt cctctgcgta tcttctcctt cttcccagtg    1440
ccagtgactg tgagagctca tctcactgga tggttgatga cacttaagaa aacctttgtt    1500
ctggcaccca gctccgtgct gcggatcatc gtcctcatca ccagccttgt ggttctgcct    1560
tacctggggg tgcatggagc cacactaggt gtgggctccc ttctagcagg gtttgtggga    1620
gagtctacca tggttgccct cgcagcatgc tatgtgtatc ggaagcagaa aaagaagatg    1680
gagaatgagt cagccaccga gggggaagac tcggccatga ccgacatgcc tccagcagag    1740
gaggtgacag acatcgtaga gatgagagag gaaaatgagt aagcacgggc caccaggggc    1800
actacaggga cagtcaggac aacagtcgtc tcttccctcc tcctcccacc aagttgtttt    1860
ctgttgttta atttttattc ttggttatga aagaggcctt gatttagagg tttcgtataa    1920
attctctagc atactgggta tgctcaccga tgcagggacc tgaagaaagg tctttactgt    1980 cgcttttgtaa ctcagaactg ctgacttcat gcccctgcct cacaaaaccc aaaagataga    2040
gctgcctctt ggccgacgtt tctaccccatt ggacaatctc cactttggaa ccaaaggact    2100
tgggctgtgc cgctgcctct tgggccagac tcttttccgt tcgtgtttgt ctcctaagaa    2160
tcaacaggtt gaagctcagc ctctcttgac ttgctcccca ataatgtggc tctaagacac    2220
gtgacccggt ggccatcaca ccccttttca ctctagagtc aagaactgtc tgcagcgccc    2280
actggtgggc cccaggctgc agcccacagt ctccctgctc ccagaggaag agctggtagc    2340
catgttgggc caacataatg ggaaatttaa tctcctgtag aaattggatc agtcacaaac    2400
tgacttgatc gccagcatct cattgttttc ctggtttcgc tgagttgcca cgcccctcgt    2460
gccg                                                               2464
```

<210> SEQ ID NO 11
<211> LENGTH: 492
<212> TYPE: PRT
<213> ORGANISM: Rattus norvegicus

<400> SEQUENCE: 11

```
Met Val Lys Phe Pro Ala Leu Thr His Tyr Trp Pro Leu Ile Arg Phe
1               5                   10                  15

Leu Val Pro Leu Gly Ile Thr Asn Ile Ala Ile Asp Phe Gly Glu Gln
            20                  25                  30

Ala Leu Asn Arg Gly Ile Ala Ala Val Lys Glu Asp Ala Val Glu Met
        35                  40                  45

Leu Ala Ser Tyr Gly Leu Ala Tyr Ser Leu Met Lys Phe Phe Ala Gly
    50                  55                  60

Pro Met Ser Asp Phe Lys Asn Val Gly Leu Val Phe Val Asn Ser Lys
65                  70                  75                  80

Arg Asp Arg Ala Lys Ala Val Leu Cys Met Val Val Ala Gly Ala Ile
                85                  90                  95

Ala Ala Val Phe His Thr Leu Ile Ala Tyr Ser Asp Leu Gly Tyr Tyr
            100                 105                 110

Ile Ile Asn Lys Leu His His Val Asp Glu Ser Val Gly Ser Lys Thr
        115                 120                 125

Arg Arg Ala Phe Leu Tyr Leu Ala Ala Phe Pro Phe Met Asp Ala Met
    130                 135                 140
```

-continued

```
Ala Trp Thr His Ala Gly Ile Leu Leu Lys His Lys Tyr Ser Phe Leu
145                 150                 155                 160

Val Gly Cys Ala Ser Ile Ser Asp Val Ile Ala Gln Val Val Phe Val
                165                 170                 175

Ala Ile Leu Leu His Ser His Leu Glu Cys Arg Glu Pro Leu Leu Ile
            180                 185                 190

Pro Ile Leu Ser Leu Tyr Met Gly Ala Leu Val Arg Cys Thr Thr Leu
        195                 200                 205

Cys Leu Gly Tyr Tyr Arg Asn Ile His Asp Ile Ile Pro Asp Arg Ser
        210                 215                 220

Gly Pro Glu Leu Gly Gly Asp Ala Thr Ile Arg Lys Met Leu Ser Phe
225                 230                 235                 240

Trp Trp Pro Leu Ala Leu Ile Leu Ala Thr Gln Arg Ile Ser Arg Pro
            245                 250                 255

Ile Val Asn Leu Phe Val Ser Arg Asp Leu Gly Gly Ser Ser Ala Ala
            260                 265                 270

Thr Glu Ala Val Ala Ile Leu Thr Ala Thr Tyr Pro Val Gly His Met
        275                 280                 285

Pro Tyr Gly Trp Leu Thr Glu Ile Arg Ala Val Tyr Pro Ala Phe Asp
        290                 295                 300

Lys Asn Asn Pro Ser Asn Lys Leu Ala Asn Thr Asn Thr Val Thr
305                 310                 315                 320

Ser Ala His Ile Lys Lys Phe Thr Phe Val Cys Met Ala Leu Ser Leu
                325                 330                 335

Thr Leu Cys Phe Val Met Phe Trp Thr Pro Asn Val Ser Glu Lys Ile
            340                 345                 350

Leu Ile Asp Ile Ile Gly Val Asp Phe Ala Phe Ala Glu Leu Cys Val
            355                 360                 365

Ile Pro Leu Arg Ile Phe Ser Phe Phe Pro Val Pro Val Thr Val Arg
370                 375                 380

Ala His Leu Thr Gly Trp Leu Met Thr Leu Lys Lys Thr Phe Val Leu
385                 390                 395                 400

Ala Pro Ser Ser Val Leu Arg Ile Ile Val Leu Ile Thr Ser Leu Val
                405                 410                 415

Val Leu Pro Tyr Leu Gly Val His Gly Ala Thr Leu Gly Val Gly Ser
            420                 425                 430

Leu Leu Ala Gly Phe Val Gly Glu Ser Thr Met Val Ala Leu Ala Ala
        435                 440                 445

Cys Tyr Val Tyr Arg Lys Gln Lys Lys Met Glu Asn Glu Ser Ala
        450                 455                 460

Thr Glu Gly Glu Asp Ser Ala Met Thr Asp Met Pro Pro Ala Glu Glu
465                 470                 475                 480

Val Thr Asp Ile Val Glu Met Arg Glu Glu Asn Glu
                485                 490
```

METHODS AND COMPOSITIONS FOR IDENTIFYING RNA-BINDING PROTEINS

CROSS-REFERENCE TO RELATED APPLICATIONS

This application is a continuation of International Patent Application No. PCT/US2004/043401, filed Dec. 22, 2004, which is entitled to priority under 35 U.S.C. §119(e), to U.S. Provisional Application No. 60/531,719, filed on Dec. 22, 2003, each of which application is hereby incorporated herein by reference in its entirety.

BACKGROUND OF THE INVENTION

In a living cell, from the moment a primary RNA transcript is complete to the actual expression of the protein encoded by the transcript, multiple cellular events and mechanisms occur, including pre-RNA splicing, RNA editing, shuttling of the mRNA between the nucleus and the cytoplasm, and ensuring the stability and translational control of the trafficked mRNAs. Each of these events provides opportunities for the cell to regulate gene expression at the RNA level.

Recent studies have revealed that RNA binding proteins (RBPs) are crucial functional components of the molecular "machinery" involved in each of these key post-transcriptional events (Maquat, L. E. et al., Cell, 104, 173-6 (2001)). Disruption of these RBPs, also known as "cellular integrators," has been implicated in the pathogenesis of epilepsy (Musunuru, K., et al., Annu. Rev. Neurosci., 24, 239-62 (2001)), rheumatism (Fritsch, R. et al., J. Immunol., 169, 1068-76 (2002)), cancer, motor neuron disease (Pellizzoni, L., et al., Cell, 95, 615-24 (1998)), and mental retardation (Turner, G., et al., Am. J. Med. Genet., 64, 196-7 (1996)). The current lack of available therapeutic tools exists, in part, because so few in vivo RNA-protein complexes have been identified and characterized. Therefore, identification of specific RNAs and the proteins with which they form ribonucleoprotein (RNP) complexes will enable the development of therapeutic tools, such as the regulation of gene expression. This will in turn enable the use of biological manipulation of gene expression in the laboratory and develop its use as a therapeutic tool for cellular processes that are not currently understood.

Several methods have previously been used to understand RNA-protein binding activity. These methods include filter binding assays, UV cross-linking assays, and gel shift assays. Gel shift assays, for example, are commonly used to confirm RNA binding activity by showing that RNA migrates at a higher molecular weight after incubation with protein, suggestive of interaction between the RNA and protein. Subsequently, a supershift assay consisting of the exposure of the RNA-protein complex, or ribonucleoprotein (RNP), to an antibody generated against the alleged RBP confirms the presence of the protein in the RNP complex when this RNP-Ab complex migrates at a rate of an even higher molecular weight species within the electrophoretic gel. The utility and applicability of the results obtained using these classical methods is limited with respect to obtaining a detailed understanding of RNA binding activity, since the methods reveal only which binding interactions occur in vitro. Other less conventional techniques have been devised to address this concern (Tenenbaum, S. A., et al., PNAS, 97, 14085-90 (2000), Brodsky, A. S., et al., Molecular & Cellular Proteomics, 1.12, 922-9 (2002)), but these methods still rely on in vitro techniques in their methodology, as is the case, for example, with the use of immunoprecipitation (IP) to assess RNA targets of embryonic lethal abnormal visual system (ELAV)-like neuronal RNA-binding protein "HuB" via cDNA arrays (Tenenbaum, S. A., et al., PNAS, 97, 14085-90 (2000)). To truly understand the dynamics of RNA-protein interactions, it is first necessary to possess the ability to identify the interactions in vivo. In an attempt to identify in vitro interactions, Miyashiro et al. have developed the APRA (antibody-positioned RNA amplification) methodology, which identifies RNA cargoes that complex in vivo with the antibody's target protein (Miyashiro, K. Y. et al., Neuron, 37, 417-31 (2003)). However, this technique also suffers from several deficiencies, including the requirement that the identity of the RNA binding protein must first be known, and unknown proteins cannot therefore be identified with the technique.

Each of these procedures permits the characterization of RNA cargoes that bind to a particular RBP. However, in order to characterize the RBPs that bind to any particular RNA, the existing methodologies are cumbersome and complex, they require a significant amount of time, they require large amounts of starting material, and they lead to many false positives. Additionally, all of the existing assays that attempt such characterization utilize in vitro methodologies. What is needed is a methodology that provides for the identification of proteins that interact in vivo with a target mRNA. Therefore, there exists a long felt need to provide a way to identify proteins that interact with a pre-selected RNA in vivo. The present invention addresses and meets this need.

BRIEF SUMMARY OF THE INVENTION

The invention features a membrane-permeable construct for transport of the construct across a lipid membrane, including a nucleic acid analog which hybridizes with an intracellular polynucleotide, the nucleic acid analog comprising at least one photoreactive moiety, a peptide moiety comprising $R_1$—CPP—$R_2$, wherein CPP is a cell-penetrating peptide, further wherein each of $R_1$ and $R_2$ are independently selected from the group consisting of a peptide, an amino acid, $NH_2$, H, or OH, further wherein the nucleic acid analog is covalently attached to one of the members selected from the group consisting of $R_1$, $R_2$, a cysteine residue within the peptide moiety, or a lysine (K) residue within the peptide moiety, and a chemical bond linking the nucleic acid analog and the peptide moiety.

In one embodiment, a membrane-permeable construct includes a CPP selected from the group consisting of SEQ ID NO:2, SEQ ID NO:6, SEQ ID NO:7, and SEQ ID NO:8. In one aspect, the membrane-permeable construct includes a CPP selected from the group consisting of a mutant, fragment, or variant of SEQ ID NO:2, SEQ ID NO:6, SEQ ID NO:7, and SEQ ID NO:8. In one embodiment, at least one of $R_1$ and $R_2$ of a peptide moiety comprises cysteine, further wherein the nucleic acid analog is disulfide bonded to the cysteine. In one aspect, a nucleic acid analog is disulfide bonded to a lysine residue of the peptide. In another aspect, a disulfide bond is disposed between a pair of cysteine residues. In yet another aspect, a C-terminal leucine residue of the peptide is amidated.

In one embodiment of the invention, a membrane-permeable construct contains a labile chemical bond. In one aspect, the labile chemical bond is selected from the group consisting of a disulfide bond, an ester bond, an avidin-biotin linkage, a cyclic unsaturated maleamate, and a 13-acylhydrazone.

In an embodiment of the invention, a membrane-permeable construct includes a nucleic acid analog selected from the group consisting of a peptide nucleic acid (PNA), a PNA/

DNA chimera, a PNA/RNA chimera, RNA, DNA, a 2'-O-alkyl RNA, a 2'-O-alkyl RNA/DNA chimera, and a nucleobase-modified oligonucleotide.

In one embodiment, a membrane-permeable construct includes a photoreactive moiety selected from the group consisting of a photoreactive amino acid, a p-benzoylbenzoyl (BzBz) moiety, an azide moiety, a 4-benzoylbenzoic acid derivative, a 4-azido-2,3,5,6,-tetrafluorobenzoic acid derivative, and an N-((2-pyridyldithio)ethyl)-4-azidosalicylamide derivative. In one aspect, a photoreactive amino acid is selected from the group consisting of para-benzoyl-L-phenylalanine (Bpa) and para-azido-L-phenylalanine (Apa).

In one embodiment, a membrane-permeable construct includes a label. In one aspect of the invention, a label is selected from the group consisting of biotin, dinitrophenyl, acridine, fluorescein, rhodamine, cyanine, digoxigenin, an intercalator, a minor-groove binder, a chemiluminescent precursor, selenium and cadmium.

The present invention also features a membrane-permeable construct for transport of the construct across a lipid membrane, including a nucleic acid analog of the structure $R_3$-Cys-PNA-Lys-amide which hybridizes with an intracellular polynucleotide, wherein $R_3$ is a photoreactive amino acid, a peptide moiety comprising $R_1$-AGYLLGKINLKA-LAALAKKIL-$R_2$ (SEQ ID NO:2), wherein $R_1$ is hydrogen and $R_2$ is $NH_2$, further wherein the nucleic acid analog is covalently attached to a cysteine residue within the peptide moiety, and a disulfide bond linking the nucleic acid analog and the peptide. In one aspect, the nucleic acid analog has the structure Bpa-Cys-PNA-Lys-amide. In another aspect, the nucleic acid analog is a PNA selected from the group consisting of SEQ ID NO:3, SEQ ID NO:4, and SEQ ID NO:5.

The present invention also features a method of identifying a protein that binds to an intracellular polynucleotide comprising a predetermined RNA sequence, the method including the steps of providing a membrane permeable construct of the invention, allowing the construct to bind with the intracellular polynucleotide to form a construct-polynucleotide complex, under conditions suitable for binding of the construct with the polynucleotide, activating the photoreactive moiety, thereby covalently cross-linking the nucleic acid analog with the protein that binds to the predetermined RNA sequence, isolating the crosslinked nucleic acid analog-protein from the cell, and identifying the protein crosslinked to the nucleic acid analog.

In one embodiment of the invention, a method includes lysing the cell containing the crosslinked nucleic acid analog-protein to form a cell lysate, contacting the cell lysate with a solid support comprising the predetermined RNA sequence under conditions suitable to allow the crosslinked nucleic acid analog-protein to bind to the solid support to form a complex, and separating the complex from the lysate. In one aspect, the isolating step includes lysing the cell containing the crosslinked nucleic acid analog-protein to form a cell lysate, contacting the cell lysate with a solid support comprising an antibody specific for at least one of the members of the group consisting of the CPP, the nucleic acid analog, the CPP-nucleic acid analog construct, and the protein that binds to the predetermined RNA sequence, under conditions suitable to allow the crosslinked nucleic acid analog-protein to bind to the antibody to form a complex, and separating the complex from said lysate. In another aspect, the PNA is selected from the group consisting of SEQ ID NO:3, SEQ ID NO:4, SEQ ID NO:5. In yet another aspect, the peptide moiety comprises SEQ ID NO:2, wherein $R_1$ is hydrogen and $R_2$ is $NH_2$, further wherein said nucleic acid analog is covalently attached to a cysteine residue within said peptide moiety.

The invention also features a kit for the identification of a protein that binds to an intracellular polynucleotide comprising a predetermined RNA sequence, including a membrane permeable construct of the invention, an applicator, and an instructional material for the use thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 is a drawing generally depicting an embodiment PNA annealing and RNA binding characterization ("PARC") technology according to the present invention. The PNA sequence illustrated in FIG. 1 is set forth in SEQ ID NO:2.

FIG. 2 illustrates the Ank mRNA sequence (SEQ ID NO:10), with the corresponding amino acid sequence (SEQ ID NO:11) shown below the nucleotide sequence. This sequence of ankylosis mRNA illustrates, in relation to the coding sequence, the location of three PNA used in various embodiments of the present invention. Ank 1 (SEQ ID NO:5) and Ank 2 (SEQ ID NO:4) PNA overlap, except for a few bases in the 3'-UTR; Ank 3 (SEQ ID NO:3) PNA, on the other hand, is located in the 5'-UTR.

DETAILED DESCRIPTION OF THE INVENTION

Figure 3:
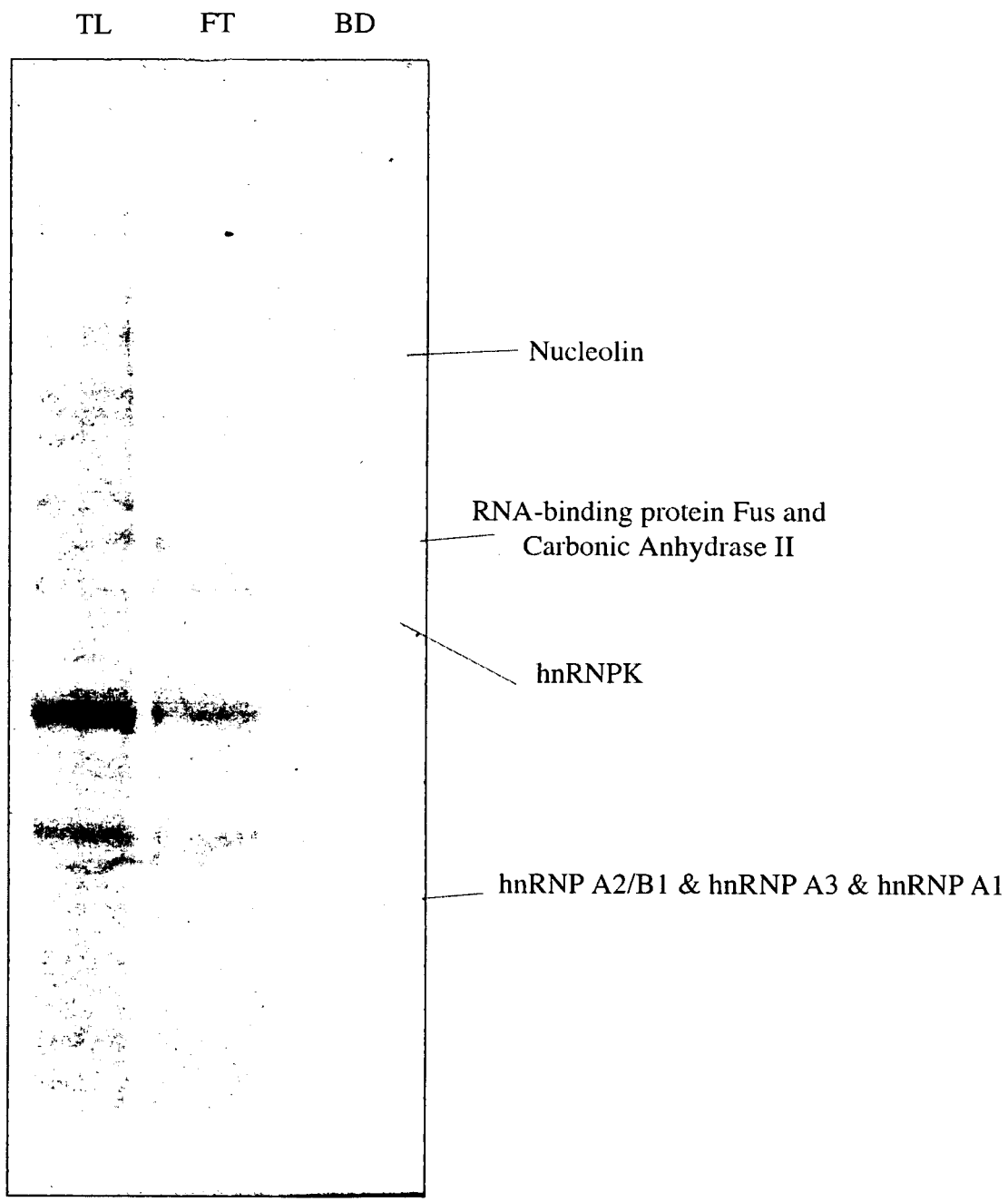
FIG. 3 is an image of a coomassie-dye stained electrophoretic gel, containing protein retrieved following BDNF treatment and "PARC" analysis (as described in FIG. 1).

RNA binding proteins (RBPs) are crucial functional components of the molecular "machinery" involved in many post-transcriptional events, and disruption of these RBPs has been implicated in the pathogenesis of a number of disease conditions. The present invention addresses the need to identify the molecular mechanism behind these conditions, and therefore identifies ways to treat these conditions by providing novel compositions and methods for such treatment.

Through the combination of cell penetrating peptide (CPP) and modified peptide nucleic acid (PNA) technologies, the present invention provides, for the first time, methods and compositions for the identification of proteins that interact in vivo with a target mRNA (FIG. 1). The present invention provides a CPP+PNA construct, further including a photoreactive label, that can be used to target, crosslink and identify the RBPs that bind to a particular RNA in vivo, through nucleic acid-like hybridization and targeted cross-linking of the CPP+PNA construct with the RBPs. Additionally, the compositions and methods of the present invention can be extended to the use of other nucleic acid analogs in addition to PNA. The present invention is also applicable to the identification of DNA-binding proteins.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

"Amplification" refers to any means by which a polynucleotide sequence is copied and thus expanded into a larger number of polynucleotide molecules, e.g., by reverse transcription, polymerase chain reaction, and ligase chain reaction, among other methods.

The term "antibody" as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

"Antisense" refers to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

By the term "applicator" as the term is used herein, is meant any device including, but not limited to, a hypodermic syringe, a pipette, and the like, for administering one or more molecules such as, but not limited to, a nucleic acid, a protein, and a small-molecule chemical moiety to a mammal.

"Binding" is used herein to mean that a first moiety physically interacts with a second moiety, wherein the first and second moieties are in physical contact with one another.

"Biological sample," as that term is used herein, means a sample obtained from or in a mammal that can be used to assess the level of expression of a nucleic acid, the level of a protein present, or both. Such a sample includes, but is not limited to, a cell, a blood sample, a neural tissue sample, a brain sample, and a cerebrospinal fluid sample.

A "cell penetrating peptide" is used herein to refer a polypeptide that facilitates the entry of said polypeptide, along with any molecule associated with the polypeptide, across one or more membranes to the interior of a cell.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g. amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

A first region of an oligonucleotide "flanks" a second region of the oligonucleotide if the two regions are adjacent one another or if the two regions are separated by no more than about 1000 nucleotide residues, and preferably no more than about 100 nucleotide residues.

A "functional fragment," as the term is used herein, refers to a fragment of a larger polypeptide or polynucleotide that retains the same activity or ability as its larger counterpart. The level of activity of a functional fragment may be the same as, less than or greater than the activity of the larger counterpart. For example, a functional fragment of the CPP transportan may be a peptide comprised of fewer amino acids than full-length transportan, but may still retain the ability to transport a cargo across a cell membrane, with a lower activity than the full-length transportan. Alternatively, a functional fragment of transportan may have a greater cargo-transport activity than full-length transportan.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is naturally-occurring.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

"Nucleic acid analogs" are structurally modified, polymeric analogs of DNA and RNA made by chemical synthesis from monomeric nucleotide analog units, and possessing some of the qualities and properties associated with nucleic acids. PNA and phosphorothioate oligonucleotides are examples of two of many nucleic acid analogs known in the art. "Watson/Crick base-pairing" and "Watson/Crick complementarity" refer to the pattern of specific pairs of nucleotides, and analogs thereof, that bind together through hydrogen-bonds, e.g. A pairs with T and U, and G pairs with C. The act of specific base-pairing is "hybridization" or "hybridizing". A hybrid forms when two, or more, complementary strands of nucleic acids or nucleic acid analogs undergo base-pairing.

"Conjugate" or "conjugated" refer to a covalent, ionic, or hydrophobic interaction whereby the moieties of a molecule are held together and preserved in proximity.

"Linker" refers to one or more atoms comprising a chain connecting a nucleic acid analog to a moiety such as a peptide, label, modifier, stabilizing group, or the like.

"Chimera" as used herein refers to an oligonucleotide including one or more nucleotide and one or more nucleotide analog units. The monomer units are linked through phosphodiester and phosphodiester analog linkages.

"Phosphodiester analog" or "internucleotide analog" refer to analogs of natural phosphodiester 3',5'-internucleotide linkages differing in their composition and/or location of attachment to a nucleotide, including but not limited to 2',5'-linkage, 3',3'-linkage, 5',5' linkage, methyl phosphonate, alkylated phosphotriester, 3'-N-phosphoramidate, and non-bridging N-substituted phosphoramidate.

The term "2'-modified RNA" means a nucleic acid analog containing one or more ribonucleotides in which a 2' position on a sugar bears a substituent replacing a hydroxyl. As an example, 2'-O-alkyl RNA comprises a nucleic acid analog containing one or more ribonucleotides in which a 2' position on a sugar consists of the moiety —OR where R is lower alkyl, such as, but not limited to, a methyl or ethyl moiety (Sproat, 1994, Protocols for Oligonucleotides and Analogs, Humana Press).

The terms "permeant" and "permeable" refer to the ability of a construct of the present invention to pass through a cellular membrane, or ascribed as characteristics of the susceptibility of cellular membranes to have constructs pass through them (Alberts et al., 1989, Molecular Biology of the Cell, 2nd Ed., Garland Publishing, New York).

"Label" refers to a group covalently attached at one or both termini of the nucleobase oligomer. The label is capable of conducting a function such as giving a signal for detection of the molecule by such means as fluorescence, chemiluminescence, and electrochemical luminescence. Alternatively, the label allows for separation or immobilization of the molecule by a specific or non-specific capture method (Andrus, 1995, PCR 2: A Practical Approach, Oxford University Press, Oxford, pp. 39-54). Labels include, but are not limited to, fluorescent dyes, such as fluorescein and rhodamine derivatives (Menchen et al., 1993, U.S. Pat. No. 5,188,934; Bergot et al., 1994, U.S. Pat. No. 5,366,860), cyanine dyes, and energy-transfer dyes (Clegg, 1992, Meth. Enzymol. 211:353-388; Cardullo et al., 1988, PNAS 85:8790-8794).

A "photoreactive label" refers to a label that becomes chemically active upon irradiation of the label with light energy. Light energy useful for activating such labels includes, but is not limited to, visible light, ultraviolet (UV) light, infrared (IR) light, among others. An activated label may contain a free radical, or other highly reactive group, and may be reactive with an adjacent molecule. By way of a non-limiting example, para-benzoylphenylalanine (BPA) is a photoreactive amino acid that may be incorporated into a peptide. Activation of BPA with UV light causes the benzoyl moiety of the amino acid to be released, leaving a phenylalanine residue containing a free radical, which is available to crosslink with other amino acids and/or proteins within proximity.

"Detection" refers to detecting, observing, or measuring a construct on the basis of the properties of a detection label.

The term "labile" refers to a bond or bonds in a molecule with the potentiality of being cleaved by reagents, enzymes, or constituents of a cell.

The term "nucleobase-modified" refers to base-pairing derivatives of A,G,C,T,U, the naturally occurring nucleobases found in DNA and RNA.

A "membrane permeable construct" refers to a molecule comprised of two or more separately-identifiable moieties, wherein the moieties have been joined together to form a single moiety, or "construct," and wherein the entire construct is membrane-permeable. That is, the entire construct has the ability to cross a lipid or cell membrane.

A photoreactive label is "incorporated into" a nucleic acid analog or a cell-penetrating peptide when the label is attached to, incorporated within, integrated into, or linked to the nucleic acid analog or the cell-penetrating peptide. This includes coupling of a label to the terminus of a nucleic acid analog or a cell-penetrating peptide as well as incorporating the label into a nucleic acid analog or a cell-penetrating peptide by including a nucleobase or amino acid analog that contains such a label.

Description

I. Nucleic Acids and Nucleic Acid Analogs
A. Nucleic Acids Encoding a Cell-Penetrating Peptide In one aspect, the present invention includes an isolated nucleic acid encoding a cell-penetrating peptide (CPP), or a functional fragment thereof, wherein the CPP comprises an amino acid sequence that confers cell-penetrating properties upon the CPP. As will be understood by one of skill in the art, a CPP has the ability to permeate a cell membrane, or be transported across a cell membrane. Further, as described elsewhere herein, a CPP has the ability to carry a cargo across a cell membrane. Such cargoes include, but are not limited to, a peptide, a nucleic acid, an a photoreactive label. Other properties of CPPs include, but are not limited to, the ability to induce endocytosis of a cargo into a cell.

The CPP transportan has been shown to infiltrate the cell (Pooga, M., FASEB J., 12, 67-77 (1998)) and also to translocate proteins such as GFP and avidin-TRITC conjugate across the cell membrane as cargos (Pooga, M., et al., FASEB J., 10, 1096 (2001)). Additionally, transportan and its analogs have been used for transport of PNA antisense oligomers (Pooga, M., et al., Nat. Biotechnol., 16, 857-61 (1998)). Therefore, in one embodiment, a CPP of the invention is TP10, the sequence of which is set forth in SEQ ID NO:1. In another embodiment of the invention, the CPP is transportan, the sequence of which is set forth in SEQ ID NO:6. In another embodiment of the invention, a CPP is penetratin (RQIKI-AFQNRRMKWKK; SEQ ID NO:7 (Derossi et al., 1994, J Biol Chem 269:10444-10450)). In yet another embodiment of the invention, a CPP is pTat (GRKKRRQRRRPPQ; SEQ ID NO:8 (Vives et al., 1997, J Biol Chem 272:16010-16017).

A nucleic acid encoding TP10 shares at least about 50% identity with a nucleic acid having the sequence of SEQ ID NO:1. Preferably, the nucleic acid is about 60% identical, more preferably, the nucleic acid is about 65% identical to SEQ ID NO:1. Preferably, the nucleic acid is about 70% identical, more preferably, the nucleic acid is about 75% identical to SEQ ID NO:1. Preferably, the nucleic acid is about 80% identical, more preferably, the nucleic acid is about 85% identical to SEQ ID NO:1. Preferably, the nucleic acid is about 90% identical, more preferably, the nucleic acid is about 95% identical to SEQ ID NO:1. Preferably, the nucleic acid is about 97% identical, more preferably, the nucleic acid is about 98% identical to SEQ ID NO:1. Preferably, the nucleic acid is about 99% identical, more preferably, the nucleic acid is about 99.9% identical to SEQ ID NO:1. Even more preferably, the nucleic acid is identical to SEQ ID NO:1, the nucleic acid encoding TP10.

The skilled artisan, when armed with the disclosure set forth herein, will know how to identify a nucleic acid encoding a TP10 useful in the present invention. Briefly, a TP10 useful in the present invention is one that can form a membrane-permeable construct when coupled with a nucleic acid analog comprising at least one photoreactive moiety. That is, any TP10 that confers the property of membrane permeability upon a TP10-nucleic acid analog-photoreactive moiety construct is encompassed by the present invention. Similarly, the skilled artisan will appreciate that a nucleic acid encoding any cell penetrating peptide that confers the property of membrane permeability upon a TP10-nucleic acid analog-photoreactive moiety construct is also included in the present invention.

B. Nucleic Acid Analogs

The present invention features a nucleic acid analog that is a peptide nucleic acid (PNA) (Nielsen, P. E., et al., Science, 254:1497-1500 (1991); Bennet, C., Biochem. Pharmacol., 55:9-19 (1998)). PNAs utilize the natural nucleobases that undergo Watson/Crick base-pairing, linked through a neutral, achiral, poly[2-aminoethylglycine] amide backbone resulting in superior hybridization properties, i.e. extremely high specificity and affinity (Egholm, M., et al., Nature, 365:566-68 (1993); Peffer, N., et al., Proc. Natl. Acad. Sci. USA, 90: 10648-52 (1993)). PNAs are not substrates for any known nucleases, proteases, peptidases, or other modifying enzymes (Demidov, V., et al., Biochem. Pharmacol., 48:1310-13 (1994)), an important property since native nucleic acids, DNA and RNA, can be rapidly degraded by nucleases (Akhtar, S., et al., Science 261:1004-12 (1991)). PNAs have been shown to block protein expression on the transcriptional and translational levels, and microinjected PNA demonstrates a strong antisense effect in intact cells (Knudsen, H., et al., Nucl. Acids Res., 24:494-500 (1996); Knudsen, H., et al., Anticancer Drug, 8:113-18 (1997)). Through hybridization to the target polynucleotide, PNA/DNA or PNA/RNA hybrid duplexes may effectively inhibit normal functioning of the intracellular DNA at the transcriptional level and RNA at the translational level. In this way, PNA binding to predetermined target sequences found within intracellular polynucleotides may be extended to identify polypeptides that are also bound to such polynucleotides. However, PNA oligomers by themselves are not efficiently delivered or transported into the cellular interior which has until now hindered the in vivo application of PNA as a means to specifically identify polynucleotide-binding proteins (Nielsen, P. E., et al., Anti-Cancer Drug Design, 8:53-63 (1993); (Hanvey, J., et al., Science 258:1481-1485 (1992); (Knudsen, H., et al., Anticancer Drug, 8:113-18 (1997)).

In one embodiment of the invention, a PNA has the sequence TACGAAACCTCTAAATCAAGG (SEQ ID NO:3), which corresponds to residues −123 to −102 of Ank mRNA. In another embodiment, a PNA has the sequence AAACCTCTAAATCAAGGCCTC (SEQ ID NO:4), corresponding to residues +1592 to +1610 of Ank mRNA. In still another embodiment of the invention, a PNA has the sequence AAGCGCGGCTGCTCTAGCAGAA (SEQ ID NO:5), corresponding to residues +1594 to +1614 of Ank mRNA.

In another embodiment of the present invention, a nucleic acid analog is a modified sugar analog. In one aspect, a sugar moiety of at least one of the nucleotides of a nucleic acid analog is modified. In one embodiment, the 2'-position of a nucleoside is modified. Oligonucleotides bearing 2'-modified nucleosides have been studied as ribozymes, nuclease-resistance antisense analogs, and other cellular mechanism probes (Lamond, A., et al., Cell, 58:383-90 (1989); (Goodchild, J., Nucleic Acids Research, 20:4607-12 (1992)). Desirable features of 2'-O-alkyl-oligoribonucleosides include high chemical stability, substantial RNA- and DNA-nuclease resistance (including RNaseH), and increased thermal duplex stability (Ohtsuka, E., et al., U.S. Pat. No. 5,013,830, issued May 7, 1991)).

In another embodiment, a fraction of the ribonucleotides of a nucleic acid analog are 2'-O-alkylribonucleotides, preferably 2'-O-methyl-ribonucleotides. Additional preferred modified ribonucleotides include 2'-O-allyl-ribonucleotides, 2'-allyl ribonucleotides, 2'-halo-ribonucleotides, 2'-O-methoxyethyl-ribonucleotides, 2'-branching group-ribonucleotides, and 2'-O-branching group-ribonucleotides.

In another embodiment of the invention, one or more nucleotides are modified at the 1'-position. In one aspect, the 1'-position includes an α-anomeric nucleotide base, in which the natural sterochemistry of the 1'-position of the sugar is inverted, i.e., the heterocycle and 5'-atom are in a trans orientation instead of a cis orientation (Morvan F., et al., Nucleic Acids Research, 14:5019-35 (1986)). The 1-position may also bear a branching group (Azhayeva, E., et al., Nucleic Acids Res., 23:1170-76 (1995)). Alternatively, the modified sugar analog is a carbocyclic-nucleotide in which the 4'-oxygen atom of the sugar is replaced with a carbon, sulfur, or nitrogen atom (Perbost et al., Biochem. Biophys. Res. Comm., 165:742-(1989)).

In another embodiment of the invention, at least two of the nucleotides making up the nucleic acid analog moiety are linked through nonstandard internucleotide linkages. By way of a non-limiting example, nonstandard internucleotide linkages include 2'-5'-linkages, inverted 3'-3' and 5'-5' linkages, methyl phosphonate, non-bridging N-substituted phosphoramidate, alkylated phosphotriester branched structures, 3'-N-phosphoramidate, peptide nucleic acid (PNA), and a non-nucleosidic polymer, among others. The term "non-nucleosidic polymer" refers to a polymer which is not a polynucleotide, e.g., polyethylene oxide, polypeptide, polyacrylamide, and polycarbohydrate.

In yet another embodiment of the present invention, at least one of the nucleotides in the nucleic acid analogs include modified nucleobases. Nucleobase modifications of the invention include, but are not limited to, C-5-alkyl pyrimidine, 2,6-diaminopurine, 2-thiopyrimidine, C-5-propyne pyrimidine, 7-deazapurine, isocytosine and isoguanine, and universal base, which shows diminished base-specific discrimination in a Watson/Crick, base-pairing hybridization interaction, e.g., 3-nitropyrrole (Nichols, R., et al., Nature, 369:492-3 (1994)) and 5-nitroindole (Loakes, D., et al., Nucleic Acids Research, 22:4039-43 (1994)).

Generally, the design and synthesis of a nucleic acid analog of the invention follows conventional teachings. By way of a non-limiting example, a nucleic acid analog is synthesized on an automated, solid-phase DNA synthesizer using phosphoramidite chemistry (Beaucage, S. L., et al., Tetrahedron, 48:2223-2311 (1992)); (Caruthers, M., et al., U.S. Pat. No.

4,415,732, issued Nov. 15, 1983); e.g. ABI 392 or 394 DNA synthesizer (PE Applied Biosystems, Foster City, Calif.), or on an automated, solid-phase peptide synthesizer, e.g. ABI 433 Peptide synthesizer (PE Applied Biosystems, Foster City, Calif.).

Nucleic acid analogs of the invention are generally synthesized using known synthetic techniques. The chemistry used to form polynucleotides is well known in the art, and can be found in such references as Beaucage, 1992. The phosphoramidite method of polynucleotide synthesis for making the nucleic acid analogs of the invention is a preferred method because of its efficient and rapid coupling and the stability of the starting nucleoside monomers. The synthesis is typically performed with the growing polymer chain attached to a solid support, so that excess reagents, which are in the liquid phase, can be easily removed by filtration, thereby eliminating the need for purification steps between cycles (Caruthers, M., et al., U.S. Pat. No. 4,458,066, issued Jul. 3, 1984).

High resolution and separation efficiency are challenging in the analysis and purification of high molecular weight molecules such as nucleic acid analogs, peptides, and constructs, which often adopt multiple, stable conformations due to charges and intramolecular hydrogen-bonding. Under the non-denaturing, reverse-phase conditions used in a conventional HPLC separation, multiple peaks may be present, complicating product identification and collection.

Therefore, in one embodiment of the invention, slab polyacrylamide gel electrophoresis (PAGE) with 7 M urea as denaturant can be used for the analysis and purification of constructs. Constructs can be isolated from an electrophoresis run by performing electrophoresis of the sample under standard conditions, excising the band after visualization under UV light, soaking in water overnight at room temperature, and desalting/concentrating on an oligonucleotide purification cartridge. Anion-exchange HPLC on a polymeric adsorbent (eg., Dionex NucleoPac PA100; 4.times.250 mm, Dionex Co.) can give good resolution, predictable elution patterns, and reproducible retention times. A useful protocol for constructs entails the following: mobile phase—solvent A: 100 mM NaCl, 10 mM NaOH in 10% acetonitrile (pH 12); solvent B: 800 mM NaCl, 10 mM NaOH in 10% acetonitrile (pH 12); elution flow rate=1.0 Ml/min; and a linear gradient from 0% B at 0 min to 80% B at 25 min (Andrus, A., et al., HPLC of Macromolecules, Oliver, R. W. A. (ed.), Oxford University Press, Oxford, pp. 141-70 (1998)). However, the present invention should not be limited to only such purification conditions as described herein. Rather, the skilled artisan, when armed with the present disclosure, will understand that other methods of isolation and purification are available. See, for example, Koch et al., 1997, J. Pept. Res. 49:80-8, which is incorporated by reference herein in its entirety.

C. Nucleic Acid Analogs with Photoreactive Labels

The present invention features a nucleic acid analog that includes at least one photoreactive label. That is, a nucleic acid analog of the invention comprises at least one photoreactive label. In one embodiment of the invention, a photoreactive label is a photoreactive amino acid. A photoreactive label of the present invention is useful for the crosslinking of a nucleic acid analog with a nucleic acid binding protein bound to the same polynucleotide to which the nucleic acid analog is bound. In one embodiment of the invention, a photoreactive label is used to crosslink a PNA with an RNA binding protein.

Examples of photoreactive labels useful for crosslinking according to the present invention include, but are not limited to, azido compounds, diazo compounds, and the like. When photoreactive labels are employed, typical crosslinking conditions comprise exposure to ultraviolet radiation at a temperature in the range of about 4° C. up to about 40° C. for a time in the range of about 0.1 minutes up to about 10 minutes, at a range of 0.1 to 100 inches from the label-containing sample. However, the invention should not be construed to be limited to these conditions, and the skilled artisan would understand, when armed with the disclosure set forth herein, that the crosslinking conditions can be varied according to the conditions and the needs for any particular set of circumstances.

By way of a non-limiting example, a photoreactive amino acid useful in the present invention includes, but is not limited to, para-benzoylphenylalanine, para-azidophenylalanine. Other photoreactive labels useful in the present invention include, but should not be construed to be limited to, a benzoylbenzoyl (BzBz) moiety, an azide moiety, 4-benzoylbenzoic acid derivatives, 4-azido-2,3,5,6,-tetrafluorobenzoic acid derivatives, and N-((2-pyridyldithio)ethyl)-4-azidosalicylamide derivatives, and the like.

A photoreactive moiety may be incorporated into a nucleic acid analog, as described in detail elsewhere herein. In one embodiment of the invention, a photoreactive moiety is chemically attached to a nucleic acid analog of the invention. In another embodiment, a photoreactive moiety is conjoined with a nucleic acid analog as part of an amino acid or peptide construct. For example, a photoreactive amino acid can be attached to a PNA through ester-mediated coupling chemistry. Alternatively, a photoreactive amino acid can be attached to a PNA through one or more amino acids to which the photoreactive amino acid is bonded. Based on the disclosure set forth herein, the skilled artisan would understand how to couple a photoreactive moiety to a nucleic acid analog, using synthetic methods well-known in the art.

A photoreactive moiety may also be incorporated into a CPP, and the CPP consequently chemically coupled with a nucleic acid analog, in order to incorporate the photoreactive moiety into a nucleic acid analog. Methods of coupling a nucleic acid analog to a CPP are described in detail elsewhere herein. A photoreactive moiety may be incorporated into a CPP by coupling the photoreactive moiety to a terminus of the CPP, to a residue sidechain in the CPP, or to the backbone of the CPP. A photoreactive moiety may also be incorporated into a CPP by including the photoreactive moiety as part of a amino acid residue, or other subunit of the CPP, thereby making the photoreactive moiety an integral part of the CPP by way of incorporation of an amino acid residue, or other subunit, into the CPP structure.

A photoreactive moiety may also be incorporated into a linker moiety used to couple a nucleic acid analog with a CPP. In one embodiment, a photoreactive moiety is contained within a linker moiety used to couple a nucleic acid analog with a CPP. The photoreactive moiety may be internally located in the linker, or the photoreactive moiety may be at one terminus of the linker. In another embodiment, a photoreactive moiety is the linker moiety used to couple a nucleic acid analog with a CPP.

In all embodiments of the invention, it will be understood that more than one photoreactive moiety may be incorporated into a nucleic acid analog, in any combination of locations within the nucleic acid analog, CPP, or the linker coupling the CPP and nucleic acid analog.

D. Other Nucleic Acids

The present invention should not be construed as being limited solely to the nucleic acid analogs, or the nucleic acids and the polypeptides encoded thereby, as disclosed herein. Once armed with the present invention, it is readily apparent to one skilled in the art that other nucleic acids can be obtained by following the procedures described herein in the experimental details section for the generation of other nucleic acid and nucleic acid analogs as disclosed herein (e.g., site-directed mutagenesis, frame shift mutations, various chemical synthetic and modifying methods, and the like), and procedures that are well-known in the art or to be developed.

Further, any other number of procedures may be used for the generation of derivative or variant forms of a CPP using recombinant DNA methodology well known in the art such as, for example, that described in Sambrook et al. (2001, Molecular Cloning: A Laboratory Manual, Cold Spring Harbor Laboratory Press, New York) and Ausubel et al. (1997, Current Protocols in Molecular Biology, Green & Wiley, New York). Procedures for the introduction of amino acid changes in a protein or polypeptide by altering the DNA sequence encoding the polypeptide are well known in the art and are also described in Sambrook et al. (2001, supra); Ausubel et al. (1997, supra).

II. Peptides and Polypeptides

The present invention includes an isolated cell-penetrating peptide (CPP). As described in detail elsewhere herein, a CPP has the ability to permeate a cell membrane, or to be transported across a cell membrane, as well as the ability to carry a cargo across a cell membrane. In one aspect of the invention, the isolated polypeptide comprising a CPP is at least about 50% identical to a polypeptide having the amino acid sequence of SEQ ID NO:2 (AGYLLGKINLKALAALAK-KIL), or a fragment thereof. Preferably, the isolated CPP is about 55% identical, more preferably, about 60% identical, more preferably, about 65% identical to SEQ ID NO:2, or some fragment thereof. Even more preferably, the isolated CPP is about 70% identical, more preferably, about 75% identical, more preferably, about 80% identical to SEQ ID NO:2, or some fragment thereof. More preferably, the isolated CPP is about 85% identical, more preferably, about 90% identical, more preferably, about 95% identical to SEQ ID NO:2, or some fragment thereof. Even more preferably, the isolated CPP is about 96% identical, more preferably, about 97% identical, more preferably, about 98% identical, and even more preferably about 99% identical to SEQ ID NO:2, or some fragment thereof. Most preferably, the portion of the isolated polypeptide comprising a CPP is SEQ ID NO:2, the amino acid sequence for TP10.

The skilled artisan, when armed with the disclosure set forth herein, will know how to identify a CPP useful in the present invention. Briefly, a CPP useful in the present invention is one that can form a membrane-permeable construct when coupled with a nucleic acid analog comprising at least one photoreactive moiety. That is, any CPP that confers the property of membrane permeability upon a CPP-nucleic acid analog-photoreactive moiety construct is encompassed by the present invention.

In one embodiment of the invention, as CPP is TP10, the sequence of which is set forth in SEQ ID NO:2. In another embodiment of the invention, a CPP is penetratin (RQIKIW-FQNRRMKWKK; SEQ ID NO:7 (Derossi et al., 1994, J Biol Chem 269:10444-10450)). In yet another embodiment of the invention, a CPP is pTat (GRKKRRQRRRPPQ; SEQ ID NO:8 (Vives et al., 1997, J Biol Chem 272:16010-16017). In general, all peptides that are referred to as CPPs or membrane translocating sequences or protein transduction domains are reviewed in (Eiriksdottir et al., 2004, Drug Delivery Reviews 1: 161-173).

In still another embodiment of the invention, a CPP is transportan (Pooga, M., et al., FASEB J., 12:67-77 (1998)). Transportan may be synthesized in whole or in part, by one or more of the methods including biological protein expression and chemical peptide synthesis, as described in detail elsewhere herein. In another embodiment, transportan may be conjugated to a nucleic acid analog, also as described elsewhere herein. The sequence of transportan is as follows:

GWTLNSAGYLLGKINLKALAALAKKIL-amide. (SEQ ID NO:6)

Transportan (galparan) is a 27 amino acid peptide from the N-terminus of the neuropeptide galanin (Bartfai, T., Raven Press, 1185 Ave of the Americas, New York, N.Y. 10036 (1995)); (Habert-Ortoli, E., et al., Proc. Natl. Acad. Sci. USA, 91:9780-83 (1994)), and mastoparan in the C-terminus, both fragments connected via a lysine. Transportan is a cell-penetrating peptide as judged by indirect immunofluorescence using the biotinylated analog, Nδ13-biotinyl-transportan. The uptake of transportan is rapid and efficient, and the internalization of biotinyl-transportan is energy independent and efficiently takes place from 0-37° C. and the maximal intracellular contraction is reached in about 20 min at 37° C. The cell-penetrating ability of transportan is not restricted by cell type, but is a general feature of the peptide sequence (for example, see Langel et al., U.S. Pat. No. 6,025,140).

However, a CPP useful in the present invention should not be limited to those disclosed herein. Rather, the skilled artisan, when armed with the present disclosure, will understand that any CPP that can transport a nucleic acid analog into a cell, known now or yet to be discovered, should be construed to be encompassed by the present invention. The present invention also provides for analogs of proteins or peptides which comprise a CPP as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "derivatives," and "variants" of the peptides of the invention (or of the DNA encoding the same) which derivatives and variants are a CPP which has been altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of a CPP of the present invention. For example, a derivative of the CPP transportan may have one or more additional amino acids added to either end of the peptide. Such biological/biochemical properties include, but are not limited to, the transport of a cargo across a cell membrane.

The present invention also includes peptides to which one or more labels have been added. A label may be used for the identification and/or purification of the peptide, or for the identification of the biological role or biological interactions of the peptide. A label useful in the present invention should have a unique or identifiable property, such as fluorecence, radioactive signal, light emission, phosphorescence, paramagnetism, and the like, which may be detectable using any spectroscopic or spectrophotometric technique known in the art. Protein labels useful in the present invention includes, but should not be limited to, biotin, dinitrophenyl, acridine, fluorescein, rhodamine, cyanine (such as Cy3 and Cy5, among others), digoxigenin, an intercalator, a minor-groove binder, a chemiluminescent precursor, selenium, cadmium, labels useful in quantum dot technology, and the like.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The peptides of the present invention may be readily prepared by standard, well-established solid-phase peptide synthesis (SPPS) as described by Stewart et al. (Solid Phase Peptide Synthesis, 2nd Edition, 1984, Pierce Chemical Company, Rockford, Ill.) and as described by Bodanszky and Bodanszky (The Practice of Peptide Synthesis, 1984, Springer-Verlag, New York). At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and coupling thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilizes tert-butyloxcarbonyl as the α-amino protecting group, and the FMOC method which utilizes 9-fluorenylmethyloxcarbonyl to protect the α-amino of the amino acid residues, both methods of which are well-known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF (hydrofluoric acid) treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequencers, which sequentially degrade the peptide and identify the amino acids in order, may also be used to determine definitely the sequence of the peptide.

Prior to its use, the peptide is purified to remove contaminants. In this regard, it will be appreciated that the peptide will be purified so as to meet the standards set out by the appropriate regulatory agencies or for specific uses. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

III. Membrane-Permeable Constructs

The present invention further includes an isolated peptide construct comprising an isolated peptide and a non-peptide moiety. The peptide portion of a construct of the invention comprises a cell-penetrating peptide (CPP). A non-peptide moiety of the present invention includes a nucleic acid analog, which further comprises a photoreactive moiety. The nucleic acid analog comprises a nucleic acid sequence that specifically binds to a predetermined intracellular nucleic acid sequence. The utility of the construct of the invention is that the CPP can carry a cargo, such as a nucleic acid-binding moiety, across a cell membrane and into a cell.

After transport of the construct across a cell membrane, and upon binding of the nucleic acid analog portion of the construct to the predetermined sequence, the photoreactive moiety of the nucleic acid analog is in close proximity to nucleic acid binding protein that is also bound to the polynucleotide comprising the predetermined nucleic acid sequence. Upon activation of the photoreactive moiety on the nucleic acid analog, the activated moiety can chemically crosslink to the nucleic acid binding protein. Specific separation of the nucleic acid analog-nucleic acid binding protein crosslinked complex can then facilitate identification of the nucleic acid binding protein.

In one embodiment of the invention, the CPP transportan is used for intracellular delivery of a PNA antisense nucleic acid analog to a specific site within progressive ankylosis mRNA within a cell ("ank," also known as "termesin"). A photoreactive amino acid adduct, p-benzyolphenylalanine (BPA), is attached to the antisense PNA, and the PNA-BPA conjugate attached to the transportan by way of a disulfide linkage. Following transport of the PNA across a cell membrane by transportan, the PNA hybridizes to the ank mRNA target. UV irradiation of the PNA-containing cell activates the BPA, causing the benzyol moiety of the BPA to be released, and creating a free phenylalanine radical that can crosslink the nearest substances, i.e. RNA binding proteins (RNPs) bound to the ank target RNA. The crosslinked PNA-RNP complex is then isolated by hybridization of a biotinylated sense oligonucleotide having a sequence that is antisense to the sequence of the PNA and coupled to streptavidin magnetic beads.

In this way, PNA annealing and RNA binding characterization ("PARC") according to the present invention provides an in vivo methodology through which a RBP that interacts with any target mRNA can be identified. By way of a non-limiting example, identifying proteins that complex with ankylosis (ank) mRNA can elucidate the mechanisms for regulation of the expression of the encoded inorganic pyrophosphate transporter.

The general conjugation strategy to prepare a construct of the invention is to synthesize the nucleic acid analog and the peptide moieties separately. Reagents and automated synthesizers are commercially available for the synthesis of peptides and nucleic acid analogs. Each moiety can be further derivatized to contain reactive functionality to form a linkage. Nucleic acid analogs can be covalently coupled to peptides through any suitable bond. In one embodiment of the invention, suitable bonds include labile bonds, such as a disulfide. To form a disulfide bond in a construct between the nucleic acid analog and peptide, the two moieties may be derivatized to contain thiol groups, one of which can contain a leaving group. In another embodiment of the invention, a linkage may be formed between a nucleic acid analog and a peptide using avidin-biotin chemistry. Methods of coupling avidin and biotin to a nucleic acid analog and a peptide are well-known in the art and will not be discussed herein.

Labile linkers allow degradation of the CPP-nucleic acid analog construct, which may be important under some conditions for reduction of unwanted effects, or for optimization of the function of the nucleic acid analog. For intracellular delivery, various labile linkers can be used. By way of a non-limiting example, disulfide bridges, pH sensitive linkers and protease/nuclease substrates can be used. The intracellular milieu is highly reducive in chemical potential, due to high (mM range) concentration of glutathione. Thiol-containing gluthathione can exist in oxidized (disulfide) or reduced (thiol) form, the ratio of which is regulated by the enzyme glutathione-S-transferase, as well as other oxidative species. Compounds containing a disulfide bond undergo reaction with reduced gluthatione, leading to a reduced disulfide bond and oxidized gluthathione. For disulfide-containing CPP conjugates, the process has been characterized by Hallbrink et al (2001, Biochim Biophys Acta. 1515:101-9).

Such constructs can cross the membrane directly over the cell membrane, or in other cases, by endocytosis. Endocytotic uptake mechanisms involve a pH drop in endocytotic vesicles after internalization. Therefore, in one embodiment of the invention, pH senstitive linkers are utilized for enhanced release of the nucleic acid analog from the CPP upon pH change. Linkers useful for this purpose include cyclic, unsaturated maleamates, and 13-acylhydrazone, among others (Fletcher et al., 2004, Org. Lett. 6:4245-4248; Braslawsky et al., 1991, Cancer Immunol Immunother. 33:367-74). In another embodiment of the invention, enzymes, such as penicillin G acylase, can be utilized to mediate separation of a CPP from a nucleic acid analog. (Grether et al., 2001, Chemistry 7:959-971.)

In another embodiment of the invention, nucleic acid analog internalization into a cell is enhanced by attachment of a moiety to a nucleic acid analog, such as PNA, that drives internalization. Such moieties include, but should not be limited to, $(Lys)_{1-4}$, CPP-(whether PNA is attached to N- or C-terminus of peptide depends on structural requirements for the CPP, and a nucleic acid analog may therefore be attached to an internal side chain in the peptide; Pooga et al., 1998, FASEB J. 12:67-77), a ligand which is internalized, a peptide or ligand attached to a nucleic acid analog by way of a disulfide bond, a nuclear localisation signal, a highly positively charged heptamer, such as PKKKRKV (SEQ ID NO:8) from the SV40 core protein. In one embodiment of the invention, $[N_{13\epsilon}\text{-Cys(Npys)}]$-Transportan is the attached moiety.

In an embodiment of the invention, a scheme for conjugation, or coupling, of the nucleic acid analog and CPP peptide moieties set forth herein, includes a nucleic acid analog derivatized with a nitropyridyl-leaving group (Npys) on a cysteine amino acid, as described in greater detail in the Experimental Examples. Displacement by the nucleic acid analog thiol of the Npys group of the peptide yields the disulfide-linked construct.

The present invention also features the intracellular delivery of hydrophilic substances, e.g. nucleic acid analogs, for the purpose of binding a predetermined nucleic acid sequence inside a cell. In one embodiment of the invention, a predetermined nucleic acid sequence is a DNA. In another embodiment of the invention, a predetermined nucleic acid sequence is an RNA. In one aspect, the RNA is progressive ankylosis phosphate transporter RNA. In another aspect, the RNA is an RNA encoding a glutamate receptor. The targeting of a photoreactive nucleic acid analog to any such RNA sequence allows for the crosslinking, isolation and identification of the proteins bound to such RNA sequences.

Therefore, the skilled artisan would understand, when armed with the disclosure set forth herein for the first time, that the present invention is useful to identify the mechanisms involved in the onset and progression of any disease or condition that is regulated post-translationally by RNA binding proteins (RBPs). Such diseases include, but are not limited to, epilepsy, rheumatism, cancer, motor neuron disease, and mental retardation. Molecular mechanisms included in this scope include, but are not limited to, ank mRNA regulation, glutamate receptor mRNA regulation, fragile X disease, epilepsy, trinucleotide repeat diseases (such as Huntington's Disease), and traumatic brain injury. The present invention therefore provides a powerful new tool for understanding and using fundamental molecular biology in order to develop novel therapeutics.

The skilled artisan will also understand that the constructs and methods described herein can be used with the cells from any living species. That is because the invention enables an improved, more efficient drug discovery, aids in identifying novel points of therapeutic intervention, and provides a generalized method for the introduction of a nucleic acid analog into essentially any cell by way of the membrane permeant activity of the CPP constructs of the invention.

IV. Vectors

In other related aspects, the invention includes an isolated nucleic acid encoding a CPP operably linked to a nucleic acid comprising a promoter/regulatory sequence such that the nucleic acid is preferably capable of directing expression of the peptide encoded by the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

Expression of a CPP, either alone or fused to a detectable tag polypeptide, in a cell can be accomplished by generating a plasmid, viral, or other type of vector comprising the desired nucleic acid operably linked to a promoter/regulatory sequence which serves to drive expression of the protein, with or without tag, in cells in which the vector is introduced. Many promoter/regulatory sequences useful for driving constitutive expression of a gene are available in the art and include, but are not limited to, for example, the cytomegalovirus immediate early promoter enhancer sequence, the SV40 early promoter, as well as the Rous sarcoma virus promoter and the like. Moreover, inducible and tissue specific expression of the nucleic acid encoding a CPP may be accomplished by placing the nucleic acid encoding a CPP, with or without a tag, under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, hormones, and the like, are also contemplated in the invention. Thus, it will be appreciated that the invention includes the use of any promoter/regulatory sequence, which is either known or unknown, and which is capable of driving expression of the desired protein operably linked thereto.

Expressing a CPP using a vector allows the isolation of large amounts of recombinantly produced protein. Further, expression of a CPP driven by a promoter/regulatory sequence can allow expression of a CPP in various cell and tissue types. Therefore, the invention includes not only methods of producing a CPP for use in the methods of the present invention, the present invention further includes methods of expression a CPP in any cell or tissue type known in the art, including eukaryotic cells, prokaryotic cells, tissue samples from eukaryotic organisms, and the like.

Selection of any particular plasmid vector or other DNA vector is not a limiting factor in this invention and a wide variety of vectors are well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The invention thus includes a vector comprising an isolated nucleic acid encoding a CPP. The incorporation of a desired nucleic acid into a vector and the choice of vectors is well-known in the art as described in, for example, Sambrook et al. (2001, Molecular. Cloning: A Laboratory Manual, Cold Spring Harbor Laboratory, New York), and in Ausubel et al. (1997, Current Protocols in Molecular Biology, John Wiley & Sons, New York).

The invention also includes cells, viruses, proviruses, and the like, containing such vectors. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The nucleic acids encoding a CPP may be cloned into various plasmid vectors. However, the present invention should not be construed to be limited to plasmids or to any particular vector. Instead, the present invention should be construed to encompass a wide plethora of vectors which are readily available and/or well-known in the art.

V. Recombinant Cells

The invention includes a recombinant cell comprising, inter alia, an isolated nucleic acid encoding a CPP, a nucleic acid encoding an antibody that specifically binds a CPP, and the like. In one aspect, the recombinant cell can be transiently transfected with a plasmid encoding a portion of the nucleic acid encoding a CPP. The nucleic acid need not be integrated into the cell genome nor does it need to be expressed in the cell. Moreover, the cell may be a prokaryotic or a eukaryotic cell and the invention should not be construed to be limited to any particular cell line or cell type. Such cells include, but are not limited to, *E. coli*, insect cells, yeast cells, and mammalian cells.

VI. Antibodies

The present invention further includes an antibody that specifically binds an CPP, a nucleic acid analog, or a CPP-nucleic acid analog construct of the present invention, or fragments thereof.

One skilled in the art would understand, based upon the disclosure provided herein, that an antibody that specifically binds CPP, a nucleic acid analog, or a CPP-nucleic acid analog construct, is useful for, inter alia, the detection of such molecules in a cell, tissue or organ. The antibody can also be used to isolate and/or purify CPP, a nucleic acid analog, or a CPP-nucleic acid analog construct. Further, once a CPP-nucleic acid analog construct has been crosslinked to an RBP by way of a photoactivatable moiety contained within the construct, an antibody can be used to isolate and/or purify the crosslinked complex.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that the CPP, nucleic acid analog, or a CPP-nucleic acid analog construct portion is rendered immunogenic (e.g., CPP conjugated with keyhole limpet hemocyanin, KLH). The chimeric proteins are produced by cloning the appropriate nucleic acids encoding, for example, CPP, a nucleic acid analog, or a CPP-nucleic acid analog construct (e.g., SEQ ID NO:2) into a plasmid vector suitable for this purpose, such as but not limited to, pMAL-2 or pCMX.

However, the invention should not be construed as being limited solely to polyclonal antibodies that bind a CPP, a nucleic acid analog, or a CPP-nucleic acid analog construct. Rather, the present invention should be construed to encompass antibodies that, among other things, bind to a CPP, a nucleic acid analog, or a CPP-nucleic acid analog construct and are able to bind these molecule when present on Western blots or in cell lysates.

One skilled in the art would appreciate, based upon the disclosure provided herein, that the antibody can specifically bind with any portion of the protein and the full-length protein can be used to generate antibodies specific therefor. However, the present invention is not limited to using the full-length molecule as an immunogen. Rather, the present invention includes using an immunogenic portion of the molecule to produce an antibody that specifically binds with a CPP, a nucleic acid analog, or a CPP-nucleic acid analog construct. That is, the invention includes immunizing an animal using an immunogenic portion, or antigenic determinant, of CPP, a nucleic acid analog, or a CPP-nucleic acid analog construct.

The antibodies can be produced by immunizing an animal such as, but not limited to, a rabbit or a mouse, with CPP, a nucleic acid analog, or a CPP-nucleic acid analog construct, or a portion thereof, or by immunizing an animal using a protein comprising at least a portion of a CPP, a nucleic acid analog, or a CPP-nucleic acid analog construct or a fusion protein including a tag polypeptide portion comprising, for example, a maltose binding protein tag polypeptide portion, covalently linked with a portion comprising the appropriate CPP, a nucleic acid analog, or a CPP-nucleic acid analog construct. The skilled artisan can also use smaller fragments of these proteins to produce antibodies that specifically bind CPP, a nucleic acid analog, or a CPP-nucleic acid analog construct.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein.

Further, the antibody of the invention may be "humanized" using the technology described in, for example, Wright et al. (1992, Critical Rev. Immunol. 12:125-168), and in the references cited therein, and in Gu et al. (1997, Thrombosis and Hematocyst 77: 755-759). The present invention also includes the use of humanized antibodies specifically reactive with epitopes of a CPP, a nucleic acid analog, or a CPP-nucleic acid analog construct. Such antibodies are capable of specifically binding a CPP, a nucleic acid analog, or a CPP-nucleic acid analog construct, or a fragment thereof. The humanized antibodies of the invention have a human framework and have one or more complementarity determining regions (CDRs) from an antibody, typically, but not limited to a mouse antibody, specifically reactive with a CPP, a nucleic acid analog, or a CPP-nucleic acid analog construct, or a fragment thereof.

When the antibody used in the invention is humanized, the antibody may be generated as described in Queen, et al. (U.S. Pat. No. 6,180,370), Wright et al., (1992, Critical Rev. Immunol. 12:125-168) and in the references cited therein, or in Gu et al. (1997, Thrombosis and Hematocyst 77(4):755-759). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as a CPP, a nucleic acid analog, or a CPP-nucleic acid analog construct, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

Human constant region (CDR) DNA sequences from a variety of human cells can be isolated in accordance with well known procedures. Preferably, the human constant region DNA sequences are isolated from immortalized B-cells as described in WO 87/02671, which is herein incorporated by reference. CDRs useful in producing the antibodies of the present invention may be similarly derived from DNA encoding monoclonal antibodies capable of binding to a CPP, a nucleic acid analog, or a CPP-nucleic acid analog construct. Such humanized antibodies may be generated using well known methods in any convenient mammalian source capable of producing antibodies, including, but not limited to, mice, rats, rabbits, or other vertebrates. Suitable cells for constant region and framework DNA sequences and host cells in which the antibodies are expressed and secreted, can be obtained from a number of sources, for example, American Type Culture Collection, Manassas, Va.

In addition to the humanized antibodies discussed above, other modifications to native antibody sequences can be readily designed and manufactured utilizing various recombinant DNA techniques well known to those skilled in the art. Moreover, a variety of different human framework regions may be used singly or in combination as a basis for humanizing antibodies directed to a CPP, a nucleic acid analog, or a CPP-nucleic acid analog construct. In general, modifications of genes may be readily accomplished using a variety of well-known techniques, such as site-directed mutagenesis (Gillman and Smith, Gene, 8:81-97 (1979); Roberts et al., 1987, Nature, 328:731-734).

Alternatively, a phage antibody library may be generated. To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (2001, Molecular Cloning: A Laboratory Manual, Cold Spring Harbor Laboratory, New York).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al. (992, Critical Rev. Immunol. 12:125-168).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CHI) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222: 581-597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

VII. Methods

The present invention is based, in part, on the novel discovery that a CPP-nucleic acid analog membrane permeable construct can be used to identify proteins that bind to a predetermined intracellular polynucleotide sequence. As described in detail elsewhere herein, a CPP-nucleic acid analog that contains one or more photoreactive groups can be used to crosslink to a protein that binds to the same predetermined intracellular polynucleotide sequence as the nucleic acid analog.

In one embodiment of the invention, a method is provided to identify a protein that binds to an RNA sequence. In another embodiment of the invention, a method is provided to identify a protein that binds to a DNA sequence.

In one embodiment, a method of identifying a protein that binds to an intracellular polynucleotide comprising a predetermined RNA sequence includes the steps of providing a membrane permeable construct to a cell under conditions suitable to allow the construct to cross the cell membrane, allowing the construct to bind with the intracellular polynucleotide to form a construct-polynucleotide complex, under conditions suitable for binding of the construct with the polynucleotide, activating a photoreactive moiety on the construct, thereby covalently cross-linking the nucleic acid analog with a protein that binds to the predetermined RNA sequence, isolating the crosslinked nucleic acid analog-protein complex from the cell, and identifying the crosslinked protein.

In one aspect of the invention, the membrane-permeable construct includes a nucleic acid analog which contains at least one photoreactive amino acid. In one aspect, the photoreactive amino acid is BPA. In another aspect of the invention, the membrane-permeable construct includes a peptide moiety of the identity R$_1$—CPP—R$_2$, wherein CPP is a cell-penetrating peptide, further wherein each of R$_1$ and R$_2$ are independently selected from the group consisting of a peptide, an amino acid, NH$_2$, H, or OH, further wherein the nucleic acid analog is covalently attached to one of the members selected from the group consisting of R$_1$, R$_2$, a cysteine residue within said peptide moiety, or a lysine (K) residue within said peptide moiety. In another aspect of the invention, the CPP is transportan. In yet another aspect of the invention, the CPP is TP10, R$_1$-AFYLLGKINLKALAALAKKIL-R$_2$ (SEQ ID NO:2), wherein R$_1$ is hydrogen and R$_2$ is NH$_2$. Other CPPs useful in the present invention are described in detail elsewhere herein.

In another aspect of the invention, the nucleic acid analog is a PNA. In another aspect, the nucleic acid analog is a PNA/DNA chimera. In yet another aspect of the invention, the nucleic acid analog is a nucleobase-modified oligonucleotide. In one embodiment of the invention, a PNA has the sequence TACGAAACCTCTAAATCAAGG (SEQ ID NO:3), which corresponds to residues −123 to −102 of Ank mRNA. In another embodiment, a PNA has the sequence AAACCTCTAAATCAAGGCCTC (SEQ ID NO:4), corresponding to residues +1592 to +1610 of Ank mRNA. In still another embodiment of the invention, a PNA has the sequence AAGCGCGGCTGCTCTAGCAGAA (SEQ ID NO:5), corresponding to residues +1594 to +1614 of Ank mRNA.

In an aspect of the invention, the nucleic acid analog is linked to the CPP moiety through a chemical bond. In one aspect, the bond is a disulfide bond. In still another aspect, a nucleic acid analog is covalently attached to a cysteine residue within the CPP moiety. Numerous other membrane permeable constructs useful in a method of the present invention are described in greater detail elsewhere herein, and will therefore not be discussed further at this point.

In another embodiment of the invention, a method of identifying a protein that binds to an intracellular polynucleotide includes particular method steps for isolation of the crosslinked nucleic acid analog-protein complex. In one aspect, the method includes lysing the cell containing the crosslinked nucleic acid analog-protein to form a cell lysate, contacting said cell lysate with a solid support comprising the predetermined RNA sequence under conditions suitable to allow the crosslinked nucleic acid analog-protein to bind to the solid support to form an additional complex, and separating the additional complex from the cell lysate. In yet another embodiment of the invention, the method includes lysing the cell containing the crosslinked nucleic acid analog-protein to form a cell lysate, contacting the cell lysate with a solid support comprising an antibody specific for at least one of the CPP, the nucleic acid analog, the CPP-nucleic acid analog construct and the protein that binds to the predetermined RNA sequence. The incubation is conducted under conditions suitable to allow the crosslinked nucleic acid analog-protein to bind to the antibody to form a complex, and separating the antibody complex from the cell lysate.

FIG. 1 depicts an embodiment of the present invention in which PNA annealing and RNA binding characterization ("PARC") is used to identify an RNA binding protein. In this embodiment, a cell-penetrating peptide-peptide nucleic acid (CPP—PNA) construct is synthesized with a photoactivatable amino acid, para-benzoylphenylalanine (BPA) attached directly to the PNA. Once the cells are exposed to the CPP—PNA, sufficient time is provided for the CPP to cross the cell membrane carrying with it the attached PNA, which will hybridize to the complimentary sequence on the target RNA. UV irradiation results in the creation of a free phenylalanine radical that crosslinks the PNA to the nearest substances, RNA binding proteins. The cells are lysed and the protein lysate is incubated with streptavidin magnetic beads previously coupled with a biotionylated oligonucleotide antisense to the PNA, thus retrieving only those proteins that are bound to the PNA. These isolated proteins are separated electrophoretically, visualized by staining with coomassie protein dye, isolated in gel slices and analyzed by mass spectrometry.

As will be understood by the skilled artisan, a method of the present invention is also amenable to the use of any solid support, based on the disclosure set forth herein, for isolation or purification of a nucleic acid analog-protein complex.

VIII. Kits

The present invention encompasses various kits for identification of a protein that binds to an intracellular polynucleotide, comprising a CTT-nucleic acid analog membrane permeable construct, an applicator, and instructional materials which describe use of the kit to perform the methods of the invention. These instructions simply embody the methods and examples provided herein. Although model kits are described below, the contents of other useful kits will be apparent to the skilled artisan in light of the present disclosure. Each of these kits is contemplated within the present invention.

The membrane permeable construct of a kit of the invention includes a CPP portion linked to a nucleic acid analog portion. In one embodiment, the CPP portion is transportan. The construct further includes a nucleic acid analog portion. In one embodiment, the nucleic acid analog portion is a PNA molecule. In one aspect, the PNA is selected from the group consisting of ACGAAACCTCTAAATCAAGG (SEQ ID NO:3), AAACCTCTAAATCAAGGCCTC (SEQ ID NO:4) and AAGCGCGGCTGCTCTAGCAGAA (SEQ ID NO:5). The construct further includes a photoreactive label. In one embodiment of the invention, the photoreactive label is a photoreactive amino acid. In one aspect, the photoreactive amino acid is part of the nucleic acid analog portion of the construct.

The membrane-permeable construct included in a kit of the present invention can be an isolated polypeptide as described elsewhere herein. Further, it will be understood that the compositions and the methods of the invention described herein are equally applicable to use in a kit of the invention.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Experimental Example 1

PNA Synthesis

PNA oligomers having the general sequence Bpa-Cys-PNA-Lys-amide were synthesised according to the protocol described by Koch et. al. (Koch T., et al., J. Pept. Res., January;49(1):80-8 (1997)). Briefly, (4-methylbenzhydrylamine (MBHA) resin was downloaded with 2-(1H-benzotriazole-1-yl)-1,1,3,3-tetramethyluronium tetrafluoroborate (TBTU)/1-hydroxybenzotriazole (Hobt) activated t-Boc-Lys-OH and subsequent acetylation to substitution 0.1 mmol/g. The t-Boc PNA monomers were assembled as N—O-(7-azabenzotriazol-1-yl)-1,1,3,3-tetramethyluronium hexafluorophosphate (HATU) esters on an Applied Biosystems 433A synthesiser in 10 µmol scale. t-Boc-Cys(4-MeBzl)-OH and t-Boc-Bpa-OH were coupled manually as TBTU esters.

The carrier peptide, TP10, was synthesised on an Applied Biosystems 431A synthesiser using t-Boc strategy and dicyclohexylcarbodiimide (DCC)/Hobt activation. The orthogonal protection group of (Pooga M., et al., Methods Mol. Biol., 208:225-36 (2002)) Lys was specifically removed after completion of main peptide chain and TBTU/Hobt activated t-Boc-Cys(Npys)-OH was coupled to the side chain.

The peptide and PNA oligomers were cleaved from resin by hydrogen fluoride at 0° C., 45 min. p-cresol or a mixture of p-cresol and p-thiocresol was used as scavenger for peptide and PNA respectively. Cleaved peptide was purified on a reverse-phase HPLC ($C_{18}$, Discovery 25 cm×21.2 mm, 5 µm, Supelco). The mass of PNA and peptide were verified by MALDI-TOF (Voyager-DE STR) mass spectrometry (FIG. 3).

1 µmol of peptide and PNA oligomer were conjugated in 100 µl dimethylsulfoxide (DMSO), 100 µl dimethylformamide and 300 µl 0.1 M acetic buffer pH 5.5. 30 µl trifluoroacetic acid was added in cases when PNA remained in pellet. The mixture was stirred at room temperature overnight and reaction products were separated on a reverse-phase HPLC $C_{18}$ column (Discovery, 25 cm×10 mm, 5 µm). The identity of each conjugate was determined by absorbance profile in a multiwavelength detector of the HPLC and MALDI-TOF mass spectrometry. The CPP—PNAs produced were as follows. "Ank3" is a PNA corresponding to residues −123 to −102 of Ank mRNA, "Ank2" is a PNA corresponding to residues +1592 to +1610 of Ank mRNA, and "Ank1" is a PNA corresponding to residues +1594 to +1614 of Ank mRNA.

As illustrated below, a disulfide bridge is formed between the N-terminal Cys of the PNA and the Cys coupled to the side chain of $Lys^7$ in TP10:

a final concentration of 20 µM and the cells were incubated for 30 minutes. In order to proceed with PARC process of the invention as described in Experimental Example 3, the DHPG-containing media was replaced with pre-warmed NB/B27. Ank RNA expression was dramatically increased in the cell soma as well as in the dendrites over a 3 hour period in the presence of BDNF at a final concentration of 50 ng/ml. For development of the results obtained using the PARC process as set forth in Experimental Example 3, 50 ng/ml BDNF was added to the NB/B27 media for 90 minutes of pre-treatment, followed by the addition of PNA, for a total BDNF treatment time of three hours.

Experimental Example 3

PARC Procedure

TP10-PNA conjugates were suspended in 1M HBS (HEPES-buffered saline), pH 7.4 at a concentration of 5 µM and stored at −20° C. until used. Cortical cells were incubated in culture with neurobasal media and B27 supplement, along with 50 nM TP10-PNA diluted in pre-warmed neurobasal media, for 90 minutes at 37° C. in 5% $CO_2$. The neurobasal media containing the PNA was aspirated from the culture dish, and ice cold 1M HBS, pH 7.4, was quickly added to the dish to wash the cells and prepare them for lysis. Prior to lysis, the cells were UV irradiated for 2.5 minutes at a distance of 2.5 inches from the UV source in order to crosslink the PNA and RNA binding proteins. The cells were then lysed.

Experimental Example 4

Cell Lysis and Isolation of Protein Lysate

The cells were lysed by removing the HBS after UV irradiation and quickly adding ice cold TX-100 lysis buffer (25

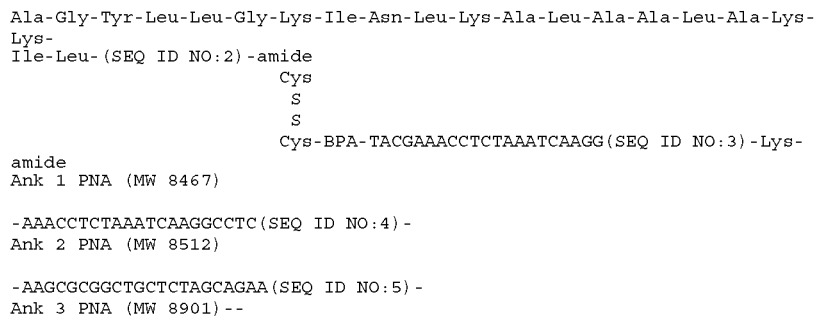

```
Ala-Gly-Tyr-Leu-Leu-Gly-Lys-Ile-Asn-Leu-Lys-Ala-Leu-Ala-Ala-Leu-Ala-Lys-
Lys-
Ile-Leu-(SEQ ID NO:2)-amide
                        Cys
                         S
                         S
                        Cys-BPA-TACGAAACCTCTAAATCAAGG(SEQ ID NO:3)-Lys-
amide
Ank 1 PNA (MW 8467)

-AAACCTCTAAATCAAGGCCTC(SEQ ID NO:4)-
Ank 2 PNA (MW 8512)

-AAGCGCGGCTGCTCTAGCAGAA(SEQ ID NO:5)-
Ank 3 PNA (MW 8901)--
```

Experimental Example 2

Cortical Cultures

Cortical cultures were maintained in NB with B27 supplement at 37° C. in 5% $CO_2$. Once the cells are of the appropriate age (7 to 22 days), they are either immediately put through the PARC procedure or pre-treated with potassium, DHPG, or BDNF Potassium stimulation of the cells was conducted by removing the NB/B27 media away from the cells and replacing it with pre-warmed 1×MAPEX solution for 5 minutes at 37° C. in 5% $CO_2$, after which the solution was removed and replaced with pre-warmed NB/B27 media. To treat cells with DHPG, a change of half of the media was performed using pre-warmed NB/B27 media. After a 30 minute incubation with the fresh media, DHPG was added to mM HEPES, pH 7.4, 0.1% triton X-100, 300 mM NaCl, 20 mM Oglycerophosphate, 1.5 mM MgCl2, 1 mM DTT, 200 nM Na3VO4, 2 mM EDTA, pH 8.0, 1 mM benzamidine, 1 mM PMSF, 2 µg/ml leupeptin, 2 µg/ml aprotinin). The cells were immediately scraped off of the plate, collected, and put on ice. Protein lysate was stored at −70° C. until used.

Experimental Example 5

Coupling of Biotinylated Sense Oligonucleotide to Streptavidin Magnetic Bead

The coupling of biotinylated sense oligonucleotide to streptavidin magnetic beads was achieved by magnetically separating 10 mg of streptavidin magnetic beads (Pure Biotech, Cat. No. MSTR0502) from the storage solution and washing twice with PBS, pH 7.4. The second PBS wash was aspirated from the beads, which were then resuspended in 1 ml PBS containing 50 µg biotinylated sense oligonucleotide. This coupling reaction was incubated on a rotating shaker at room temperature for 1 hour. Following magnetic separation, the bead-streptavidin-biotin-oligo complex was washed with PBS, pH 7.4. The wash step was repeated five times to remove any unbound biotinylated oligonucleotide. The last PBS wash was aspirated off, and the beads were either resuspended at 10 mg/ml in storage buffer (10 mg BSA and 2 mg $NaN_3$ in 10 ml PBS, pH 7.4) or resuspended at 10 mg/ml in TX-100 lysis buffer if they were to be used immediately. Oligo coupled beads were stored at 4° C. until ready to use, at which point they were magnetically separated from the storage solution and resuspended in TX-100 lysis buffer at 10 mg/ml.

Experimental Example 6

Isolation of RBPs from Total Protein Lysate

An aliquot of total lysate is kept at −70° C. for gel analysis; the rest of the lysate was rotated for 1 hour at room temperature with 100 µg magnetic beads previously coupled to the sense oligo. The flowthrough was removed (an aliquot was saved for future gel analysis) following magnetic separation. The beads should now be hybridized to the PNA crosslinked to RBPs. The bead-oligo-PNA-RBP complex was washed twice with TX-100 buffer to remove any unbound PNA-RBP. Protease inhibitors were added to a pre-warmed salt-free version of TX-100 lysis buffer, and the proteins are eluted from the magnetic beads by rotating at RT/37° C./50° C. for 20 minutes with 30 µl of this pre-warmed salt-free buffer.

Experimental Example 7

Gel Electrophoresis and Staining

Polyacrylamide gel electrophoresis was performed on the total lysate, flowthrough, and bound protein using NuPAGE 10% Bis-Tris Gels (Invitrogen, Cat. Nos. NP0301-3). To examine the results obtained using the PARC protocol, the Biorad Silverstain Plus Kit (Biorad Cat. No. 161-0449) was used to visualize the protein. Once the optimal conditions were determined using the more sensitive silver stain, visualization of bound protein was carried out using coomassie blue protein staining prior to mass spectometry. Protein gels were incubated at room temperature, with shaking, in a fixative (46% methanol, 7% acetic acid) for one hour, followed by one hour in stain (46% methanol, 7% acetic acid, filter-sterilized 0.1% Coomassie Stain Brilliant Blue R-250), and then were de-stained in 5% methanol, 7.5% acetic acid until protein bands could be detected. At that point, the gels were transferred into a 5% acetic acid stop solution. Bands that illustrated enrichment in the bound protein were then extracted from the gel, and the gel slices were put into 1-2% acetic acid and stored at −20° C. until mass spectrometry was performed.

Figure 4:
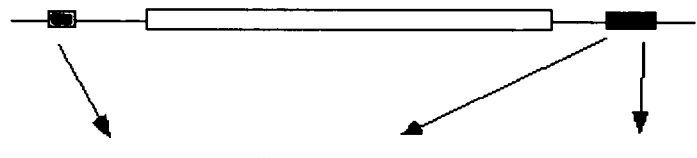
FIG. 4 is a condensed table illustrating the identification of RNA binding proteins using PNA—CPP constructs directed to three different regions of Ank mRNA. "No Treatment"=no treatment of the cells containing the PNA—CPP construct; "DHPG"=treatment of the cells containing the PNA—CPP construct with 20 μM DHPG; "K+"=treatment of the cells containing the PNA—CPP construct with 3 mM potassium; and "BDNF"=treatment of the cells containing the PNA—CPP construct with 50 ng/ml BDNF). "Ank3" is a PNA corresponding to residues −123 to −102 of Ank mRNA, "Ank2" is a PNA corresponding to residues +1508 to +1525 of Ank mRNA, and "Ank1" is a PNA corresponding to residues +1594 to +1614 of Ank mRNA.

Numerous proteins have been isolated in complex with Ank mRNA using this technology set forth herein in the present invention. The isolated proteins were identified using mass spectometry; some of these proteins, such as hnRNP K and nucleolin, were previoiusly shown to demonstrate RNA-binding activity. Nucleolin, unlike any other protein identified by a PARC method of the present invention, has been isolated with each PNA used herein and under every pre-treatment condition. The functional significance of this finding suggests that this ubiquitous property relates to a prominent role for nucleolin in the regulation of Ank expression. Other proteins have been isolated only in complex with one or two of the PNAs disclosed herein, but not all three. HnRNP K has been found only in conjunction with the Ank 1 PNA and hnRNP U only with Ank 2 PNA and Ank 3 PNA (FIGS. 3, 4 and 4A).

FIG. 3 demonstrates the results of a coomassie-dye stained electrophoretic gel, containing protein retrieved following BDNF treatment and "PARC" analysis (as described in FIG. 1). Ten day old cortical cells were treated with 50 ng/ml BDNF from 90 minutes before 50 nM Ank 1 PNA was added for an additional 90 minutes. The cells were subsequently UV irradiated, lysed, and the bound protein was retrieved by streptavidin magnetic beads coupled to the antisense-PNA biotinylated oligonucleotide. The total lysate (TL), the flowthrough (FT), and the bound protein were separated by SDS-PAGE and Coomassie stained. Enriched bands (as illustrated) were isolated, proteolyzed, and identified via mass spectometry.

The coexistence of ank RNA with nucleolin protein was confirmed by simultaneous fluorescent in situ hybridization for ank RNA and fluorescence immunohistochemistry for nucleolin. Nucleolin antibody was applied to fixed cortical neurons. The binding of the antibody was detected using fluorescence. The in situ hybridization was performed with a mixture of short fluorescence-tagged oligonucleotides that bind to different regions of the Ank RNA. The fluorochrome used for each region was different so that the antibody staining appeared green and the RNA appeared red, and so that co-existent entities appeared in yellow.

Table 1 illustrates the RNA binding proteins that bind to each PNA (Ank 1, Ank 2, and Ank 3) as a function of pharmacological stimulation, according to the methods and compositions of the present invention. These data demonstrate that more RBPs bind to the 3' end of ank RNA than to other regions and that this binding can be pharmacologically regulated.

TABLE 1

Identification of RNA binding proteins using PNA-CPP constructs directed to three different regions of Ank mRNA.

|  | Ank 1 | Ank 2 | Ank 3 |
| --- | --- | --- | --- |
| None | Nucleolin (4) | Nucleolin (3) | Nucleolin (3) |
|  | hnRNP A1 (1) |  |  |
|  | hnRNP A2/B1 (1) | hnRNP A2/B1 (1) |  |
|  |  | hnRNP A3 (1) |  |
|  | hnRNP K (2) |  |  |
|  | hnRNP L (1) |  |  |
|  |  | hnRNP R (1) |  |
|  |  | hnRNP U (2) | hnRNP U (1) |
|  | hnRNP X (1) |  |  |
|  | hsp90-a (1) |  |  |
|  | hsp90-b (1) |  |  |

TABLE 1-continued

Identification of RNA binding proteins using PNA-CPP constructs directed to three different regions of Ank mRNA.

| | Ank 1 | Ank 2 | Ank 3 |
|---|---|---|---|
| | hscognate 90 (1)<br>hsp82 (1)<br>hsp71 (1)<br>hsp70 (1)<br>MARTA 1 (1) | | |
| | | splcing factor Prp8 (1)<br>SAP 114 (1)<br>TAR RBP (1) | TAR RBP (1)<br>U5snRNP (1) |
| Potassium | Nucleolin (2)<br>hnRNP K (1) | | Nucleolin (2) |
| | | | hsp70 (1)<br>hsp71 (1)<br>hsp90-a (1) |
| | hsp90-b (1)<br>hscognate 90 (1)<br>hspHPTG (1) | | hsp90-b (1)<br>hscognate 90 (1)<br>hspHPTG (1) |
| DHPG | Nucleolin (2)<br>hnRNP K (1)<br>hnRNP L (1)<br>hsp90-b (1)<br>hscognate 90 (1)<br>hspHPTG (1) | | |
| BDNF | Nucleolin (3)<br>hnRNP A1 (3)<br>hnRNP A2/B1 (3)<br>hnRNP A3 (2)<br>hnRNP K (2) | nucleolin | nucleolin |
| | | hnRNP U (1) | hnRNP U (1) |
| | hnRNP X (2)<br>pre-mRNA splc fac75 (1)<br>PTB-assoc splicing factor (PSF) (2)<br>RBP Fus (pigpen) (3)<br>spliceosome associated<br>prot 145 (SAP145) (2) | | |

Table legend:
"none" = no treatment of the cells containing the PNA-CPP construct;
"DHPG" = treatment of the cells containing the PNA-CPP construct with 20 μM DHPG;
"potassium" = treatment of the cells containing the PNA-CPP construct with 3 mM potassium; and
"BDNF" = treatment of the cells containing the PNA-CPP construct with 50 ng/ml BDNF).
"Ank3" is a PNA corresponding to residues −123 to −102 of Ank mRNA,
"Ank2" is a PNA corresponding to residues +1592 to +1610 of Ank mRNA, and
"Ank1" is a PNA corresponding to residues +1594 to +1614 of Ank mRNA.

Experimental Example 8

Conjugation of PNA to a Cell-Penetrating Peptide using a Disulfide Bond

To obtain heterodimeric disulfide bridge between a PNA and a cell penetrating peptide, the cysteine residue of one component, either PNA or peptide, must be derivatized. 3-Nitro-2-pyridinesulphenyl (NPys)-derivatised Cys is specifically reactive towards free thiols. Npys labelled Cys is commercially available and can be assembled into peptide chain like a commonly protected amino acid.

First, 1 molar equivalent (0.5-2 mg) of peptide and 1 molar equivalent of PNA are prepared in separate microcentrifuge tubes. The coupling efficiency varies between sequences of both PNA and peptide, and depends on solubility and purity of each. Therefore, a 1:1 molar ratio may not be optimal in every case, and optimization of the ratio will be required to achieve the desired results. PNA is dissolved in 200 μl deoxygenated DMSO. Peptide is dissolved in 100 μl of 0.01 M acetic buffer pH 5.5, and 200 μl of DMF is added to both of the solutions. The two solutions are mixed and vortexed thoroughly. The mixture is stirred overnight, or at least for 4 hours, at room temperature, shielded from light.

Reaction products can be separated by semipreparative RP-HPLC. A C-18 column, or the column used for purification of the peptide, if different, is used. An isocratic gradient can be used, for example, 20% eluent A for 5 min, followed by gradual increase of eluent A to 100% in 40 min. 20% acetonitrile will prevent "unreacted" PNA from interacting with the stationary phase in the column, and unreacted PNA will be washed out of the column together with solvents (DMSO and DMF). Conjugated PNA precedes the peptide peak. Detection wavelengths used include: 218 nm (absorbance maximum for peptide bond) and 260 nm (PNA nucleobases). For single wavelength detector, 260 nm is used for detection. Fractions absorbing both wavelengths are collected.

Fraction(s) are freeze-dried and stored in the dark at −20° C. Mass spectrometry analysis of the conjugate may be used to further verify the desired product. Care must be taken as not to reduce the disulfide bridge during preparation of a sample or collection of mass spectrometric data.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. An in vitro method of identifying a protein that binds to a predetermined RNA sequence in a cell, said method comprising the steps of:
   a) providing a membrane permeable construct to a cell under conditions suitable for transport of said construct across the membrane of said cell, wherein said construct comprises:
   i) a nucleic acid analog which hybridizes with an untranslated region of an intracellular polynucleotide comprising a predetermined target mRNA sequence, said nucleic acid analog further comprising at least one photoreactive moiety;
   ii) a peptide moiety comprising $R_1$-CPP-$R_2$, wherein CPP is a cell-penetrating peptide, further wherein each of $R_1$ and $R_2$ are independently selected from the group consisting of a peptide, an amino acid, $NH_2$, H, or OH, further wherein said nucleic acid analog is covalently attached to one of the members selected from the group consisting of $R_1$, $R_2$, a cysteine residue within said peptide moiety, or a lysine (K) residue within said peptide moiety; and
iii) a chemical bond linking said nucleic acid analog and said peptide moiety;
b) incubating said construct with said cell under conditions suitable to allow said construct to bind with an untranslated region of an intracellular polynucleotide comprising a predetermined target mRNA sequence through a Watson/Crick base-pair binding between said nucleic acid analog and said untranslated region of said target mRNA sequence to form a construct-polynucleotide complex in said cell;
c) activating said photoreactive moiety of said construct, thereby covalently cross-linking said nucleic acid analog with a nearby RNA binding protein that binds to said predetermined target mRNA sequence;
d) isolating said crosslinked nucleic acid analog-protein from said cell following step c); and
e) identifying said protein crosslinked to said nucleic acid analog; thereby identifying a protein that binds to a predetermined target RNA sequence.

2. The method of claim 1, wherein said isolating in step d) comprises:
i) lysing the cell containing the crosslinked nucleic acid analog-protein to form a cell lysate;
ii) contacting said cell lysate with a solid support comprising said predetermined RNA sequence under conditions suitable to allow said crosslinked nucleic acid analog-protein to bind to said solid support to form a complex; and
iii) separating said complex from said lysate.

3. The method of claim 1, wherein said isolating step d) comprises:
i) lysing the cell containing the crosslinked nucleic acid analog-protein to form a cell lysate;
ii) contacting said cell lysate with a solid support comprising an antibody specific for at least one of the members of the group consisting of:
A) the CPP;
B) the nucleic acid analog;
C) the CPP-nucleic acid analog construct; and
D) the protein that binds to the predetermined RNA sequence;
under conditions suitable to allow said crosslinked nucleic acid analog-protein to bind to said antibody to form a complex; and
iii) separating said complex from said lysate.

4. The method of claim 1, wherein said nucleic acid analog is a peptide nucleic acid (PNA), further wherein said PNA is selected from the group consisting of:
a) TACGAAACCTCTAAATCAAGG (SEQ ID NO:3);
b) AAACCTCTAAATCAAGGCCTC (SEQ ID NO:4); and
c) AAGCGCGGCTGCTCTAGCAGAA (SEQ ID NO:5).

5. The method of claim 1, wherein said peptide moiety comprises $R_1$- AGYLLGKINLKALAALAKKIL-$R_2$ (SEQ ID NO:2), wherein $R_1$ is hydrogen and $R_2$ is $NH_2$, further wherein said nucleic acid analog is covalently attached to a cysteine residue within said peptide moiety.

* * * * *